United States Patent
Allen

(10) Patent No.: US 10,828,379 B2
(45) Date of Patent: *Nov. 10, 2020

(54) IN VIVO DIFFERENTIATION OF RELATIVE OXYGEN LEVELS AND TUMOR NECROSIS USING DIVALENT EUROPIUM

(71) Applicant: WAYNE STATE UNIVERSITY, Detroit, MI (US)

(72) Inventor: Matthew J. Allen, Plymouth, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 893 days.

This patent is subject to a terminal disclaimer.

(21) Appl. No.: 15/067,901

(22) Filed: Mar. 11, 2016

(65) Prior Publication Data

US 2016/0263252 A1 Sep. 15, 2016

Related U.S. Application Data

(60) Provisional application No. 62/131,601, filed on Mar. 11, 2015.

(51) Int. Cl.
*A61B 5/055* (2006.01)
*A61K 49/10* (2006.01)

(52) U.S. Cl.
CPC ................. *A61K 49/106* (2013.01)

(58) Field of Classification Search
None
See application file for complete search history.

(56) References Cited

U.S. PATENT DOCUMENTS

| 2009/0074833 A1* | 3/2009 | Whiteford | C08K 5/0008 |
| | | | 424/423 |
| 2013/0078189 A1 | 3/2013 | Allen et al. | |
| 2016/0022842 A1* | 1/2016 | Allen | A61K 9/127 |
| | | | 424/9.321 |

FOREIGN PATENT DOCUMENTS

WO 2014/164712 A1 10/2014

OTHER PUBLICATIONS

Konstantinidis et al. (Aerterioscler Thromb Vasc Biol. 2012, 32, pp. 1-20).*
Joel Garcia et al., Physical Properties of Eu2+-Containing Cryptates as Contrast Agents for Ultrahigh-Field Magnetic Resonance Imaging; 2012 European Journal of Inorganic Chemistry; 6 Pages.

* cited by examiner

*Primary Examiner* — Michael G. Hartley
*Assistant Examiner* — Melissa J Perreira
(74) *Attorney, Agent, or Firm* — Brooks Kushman P.C.

(57) ABSTRACT

A method of magnetic resonance imaging a target tissue in a subject includes a step of administering a first $Eu^{2+}$-containing complex to the subject. The first $Eu^{2+}$-containing complex has a reduction potential that is more negative than a reduction potential for a selected compound present in the target tissue. A first set of images of the target tissue in the subject is then taken by $T_1$-weighted magnetic resonance imaging.

18 Claims, 11 Drawing Sheets

| Reaction | $E^\circ$ (V) | $E^{\circ'}$ (V) |
|---|---|---|
| $O_2 + 4H^+ + 4e^- \rightleftharpoons 2H_2O$ | +1.229 | +0.816 |
| $Fe^{3+} + e^- \rightleftharpoons Fe^{2+}$ | +0.771 | +0.771 |
| $I_2 + 2e^- \rightleftharpoons 2I^-$ | +0.535 | +0.535 |
| Cytochrome $a$ ($Fe^{3+}$) + $e^- \rightleftharpoons$ cytochrome $a$ ($Fe^{2+}$) | +0.290 | +0.290 |
| $O_2(g) + 2H^+ + 2e^- \rightleftharpoons H_2O_2$ | +0.695 | +0.281 |
| Cytochrome $c$ ($Fe^{3+}$) + $e^- \rightleftharpoons$ cytochrome $c$ ($Fe^{2+}$) | ——— | +0.254 |
| 2,6-Dichlorophenolindophenol + $2H^+$ + $2e^- \rightleftharpoons$ reduced 2,6-Dichlorophenolindophenol | ——— | +0.22 |
| Dehydroascorbate + $2H^+$ + $2e^- \rightleftharpoons$ ascorbate + $H_2O$ | +0.390 | +0.058 |
| Fumarate + $2H^+$ + $2e^- \rightleftharpoons$ succinate | +0.433 | +0.031 |
| Methylene blue + $2H^+$ + $2e^- \rightleftharpoons$ reduced product | +0.532 | +0.011 |
| Glyoxylate + $2H^+$ + $2e^- \rightleftharpoons$ glycolate | ——— | -0.090 |
| Oxaloacetate + $2H^+$ + $2e^- \rightleftharpoons$ malate | +0.330 | -0.102 |
| Pyruvate + $2H^+$ + $2e^- \rightleftharpoons$ lactate | +0.224 | -0.190 |
| Riboflavin + $2H^+$ + $2e^- \rightleftharpoons$ reduced riboflavin | ——— | -0.208 |
| $FAD + 2H^+ + 2e^- \rightleftharpoons FADH_2$ | ——— | -0.219 |
| $(Glutathione-S)_2 + 2H^+ + 2e^- \rightleftharpoons$ 2 glutathione-SH | ——— | -0.23 |
| Safranine T + $2e^- \rightleftharpoons$ leucosafranine T | -0.235 | -0.289 |
| $(C_6H_5S)_2 + 2H^+ + 2e^- \rightleftharpoons 2C_6H_5SH$ | ——— | -0.30 |
| $NAD^+ + H^+ + 2e^- \rightleftharpoons NADH$ | -0.105 | -0.320 |
| $NADP^+ + H^+ + 2e^- \rightleftharpoons NADPH$ | ——— | -0.324 |
| Cystine + $2H^+$ + $2e^- \rightleftharpoons$ 2 cysteine | ——— | -0.340 |
| Acetoacetate + $2H^+$ + $2e^- \rightleftharpoons$ L-β-hydroxybutyrate | ——— | -0.346 |
| Xanthine + $2H^+$ + $2e^- \rightleftharpoons$ hypoxanthine + $H_2O$ | ——— | -0.371 |
| $2H^+ + 2e^- \rightleftharpoons H_2$ | 0.000 | -0.414 |
| Gluconate + $2H^+$ + $2e^- \rightleftharpoons$ glucose + $H_2O$ | ——— | -0.44 |
| $O_2$ to superoxide | ——— | -0.45 |
| $SO_4^{2-} + 2e^- + 2H^+ \rightleftharpoons SO_3^{2-} + H_2O$ | ——— | -0.454 |
| $2SO_3^{2-} + 2e^- + 4H^+ \rightleftharpoons S_2O_3^{2-} + 2H_2O$ | ——— | 0.527 |

*Fig. 1*

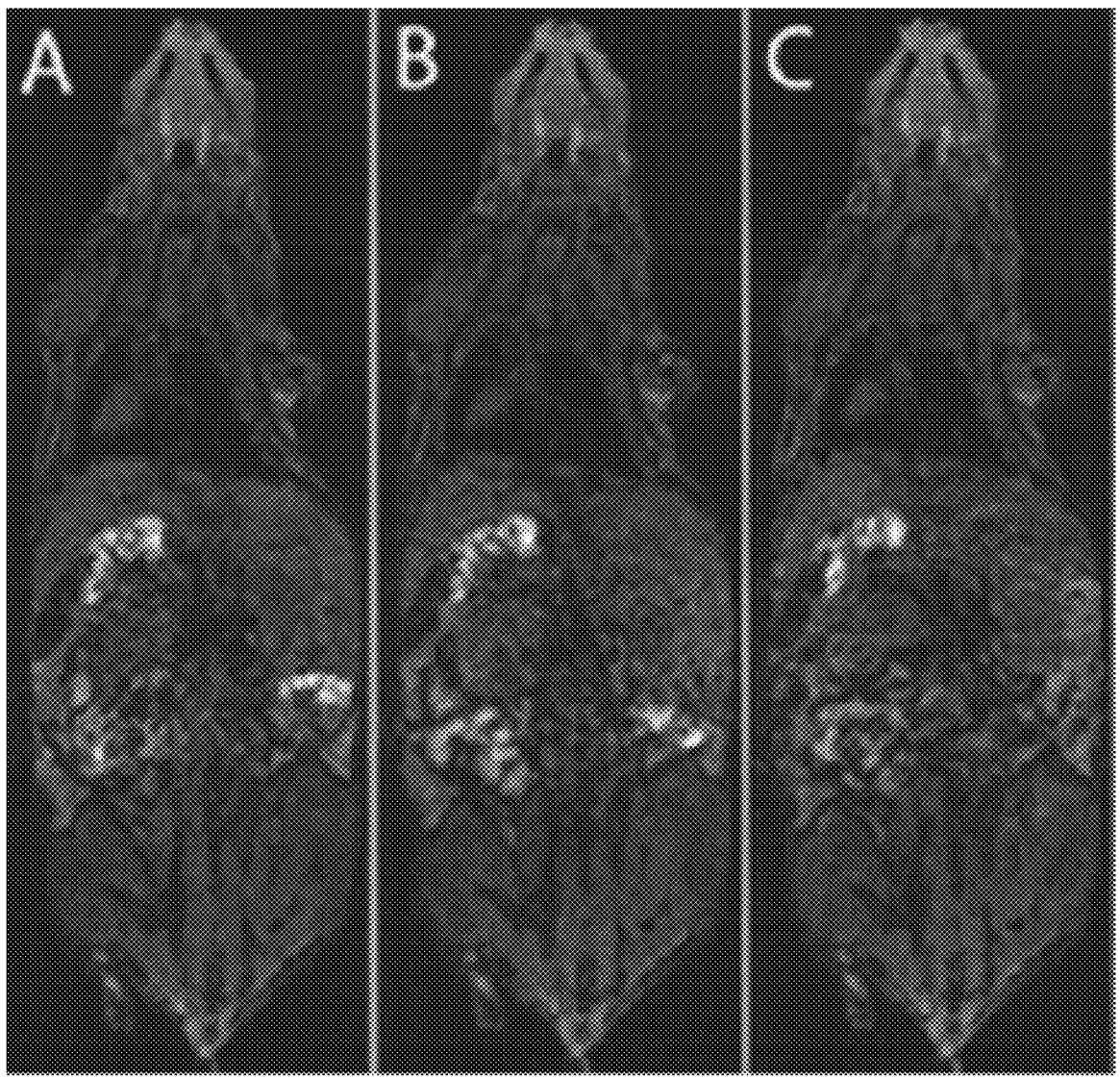
*Fig. 7A*  *Fig. 7B*  *Fig. 7C*

IN VIVO DIFFERENTIATION OF RELATIVE OXYGEN LEVELS AND TUMOR NECROSIS USING DIVALENT EUROPIUM

CROSS-REFERENCE TO RELATED APPLICATIONS

This application claims the benefit of U.S. provisional application Ser. No. 62/131,601 filed Mar. 11, 2015, the disclosure of which is hereby incorporated in its entirety by reference herein.

STATEMENT REGARDING FEDERALLY SPONSORED RESEARCH OR DEVELOPMENT

The invention was made with Government support under Contract No. R01EB013663 awarded by the National Institutes of Health. The Government has certain rights to the invention.

TECHNICAL FIELD

In at least one aspect, the present invention is related to magnetic resonance imaging contrast agents.

BACKGROUND

Redox environments are critical to the homeostasis of living organisms, and redox stress is associated with ailments including cancer and diseases such as cardiovascular, Alzheimer's, fatty liver, and chronic kidney. The ability to detect specific changes in redox environments would be invaluable to diagnosing diseases and monitoring responses to therapies. Consequently, considerable research effort has focused on developing systems to measure changes in redox environment through the use of polarography, histological staining, electron paramagnetic resonance oximetry, fluorescence microscopy, positron emission tomography, single-photon emission computed tomography, and magnetic resonance imaging (MRI). Despite numerous advances, a general approach remains elusive because redox environments are a complicated balance of redox-active species including glutathione, ascorbate, urate, nicotinamide adenine dinucleotides, tocopherols, thioredoxin, hydrogen peroxide, and oxygen.

Accordingly, there is a need for the development of alternative MRI contrast agents such as divalent europium-containing complexes as set forth below.

SUMMARY

The present invention solves one or more problems of the prior art by providing in at least one embodiment, a method of magnetic resonance imaging a target tissue in a subject. The method includes a step of administering a first $Eu^{2+}$-containing complex to the subject. Characteristically, the first $Eu^{2+}$-containing complex has a reduction potential that is more negative than a reduction potential for a selected compound present in the target tissue. A first set of images of the target tissue in the subject is taken by $T_1$-weighted magnetic resonance imaging.

In another embodiment, a method of magnetic resonance imaging a target tissue in a subject is provided. The method includes a step of administering a first $Eu^{2+}$-containing complex to the subject. The first $Eu^{2+}$-containing complex has a reduction potential that is more negative than a reduction potential for a selected compound present in the target tissue. A first set of images of the target tissue in the subject is taken by $T_1$-weighted magnetic resonance imaging. A second $Eu^{2+}$-containing complex is administered to the subject. The second $Eu^{2+}$-containing complex has a reduction potential that is more positive than a reduction potential for the selected compound present. A second set of images of the target tissue in the subject is taken by $T_1$-weighted magnetic resonance imaging. The first set of images and the second set of images are compared to identify regions that possess different concentrations of the selected compound.

BRIEF DESCRIPTION OF THE DRAWINGS

FIG. 1. Table 1 providing compounds of biological interest and the related redox reactions. $E°$ is the standard reduction potential and $E°{'}$ is the standard reduction potential at pH 7.

1239-1253. DOI: 10.1111/j.1582-4934.2011.01258.x; Golub A S, Barker M C, Pittman R N. Po$_2$ profiles near arterioles and tissue oxygen consumption in rat mesentery. Am. J. Physiol. Heart Circ. Physiol. 2007; 293: H1097-H1106. DOI: 10.1152/ajpheart.00077.2007).

FIGS. 7A-I. Representative T$_1$-weighted images demonstrating the response of Eu$^{II}$-222 after different injection types. The images are (A) pre-intravenous injection; (B) 3 min post-intravenous injection; (C) 8 min post-intravenous injection; (D) pre-intraperitoneal injection; (E) 3 min post-intraperitoneal injection; (F) 8 min post-intraperitoneal injection; (G) pre-subcutaneous injection; (H) 3 min post-subcutaneous injection; and (I) 8 min post-subcutaneous injection. Red arrows denote areas of positive contrast enhancement. The area represented by each image is 31 mm×90 mm.

Figure 8:
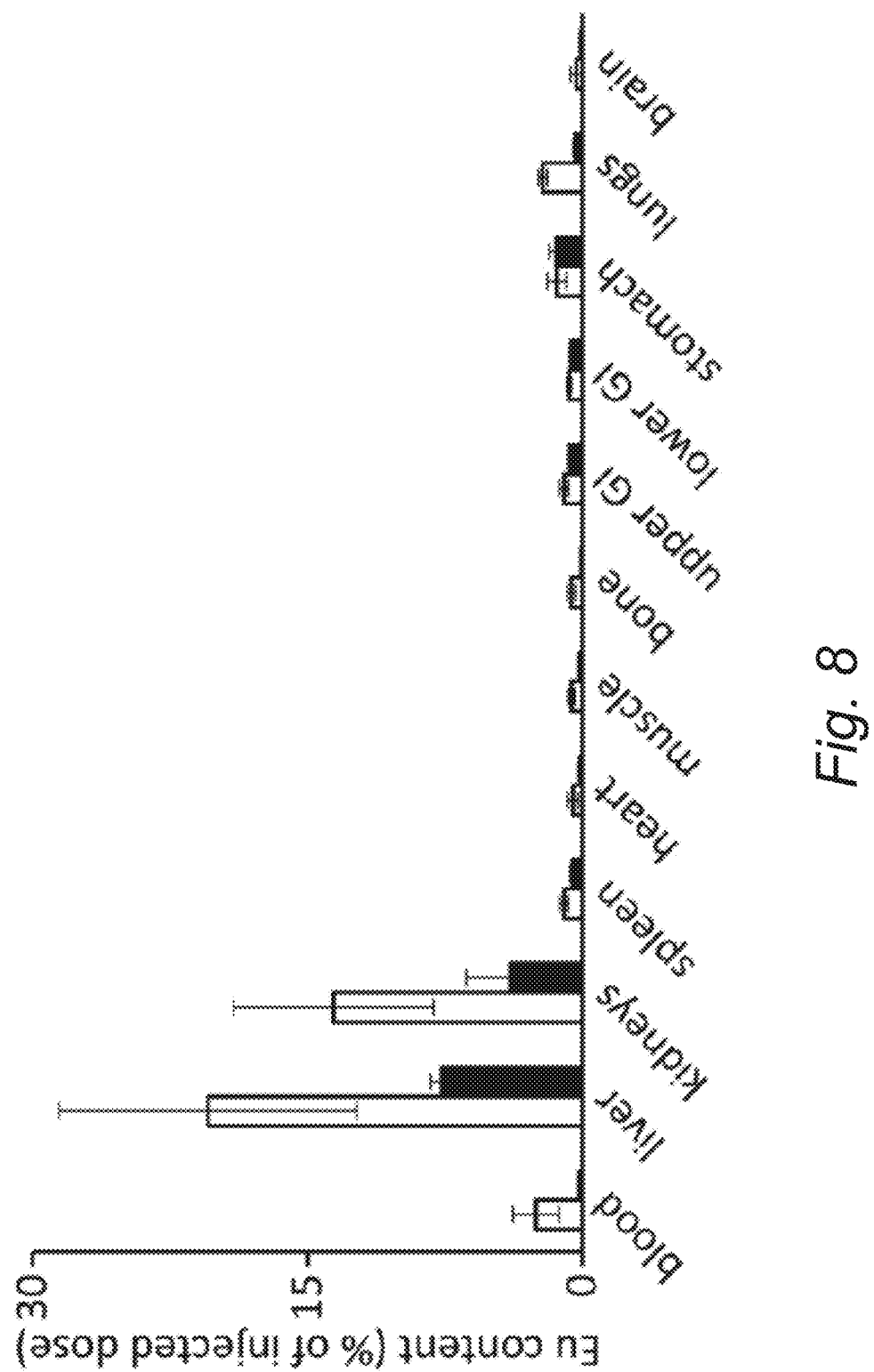

FIG. 8. Percent of injected dose of europium retained per organ 1 h post-injection for intravenous (white bars) and intraperitoneal (black bars) injections. Error bars represent the standard error of the mean of 3 independent experiments.

DETAILED DESCRIPTION

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property. Unless stated to the contrary, all R groups include H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, or $C_{5-14}$ heteroaryl.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "alkyl", as used herein, unless otherwise indicated, includes $C_{1-12}$ saturated monovalent hydrocarbon radicals having straight or branched moieties, including, but not limited to, methyl, ethyl, n-propyl, iso-propyl, n-butyl, sec-butyl, tert-butyl, and the like.

The term "alkenyl", as used herein, unless otherwise indicated, includes $C_{2-12}$ alkyl groups, as defined above, having at least one carbon-carbon double bond, such as —CH$_2$—CH=CH$_2$.

The term "alkynyl", as used herein, unless otherwise indicated, includes $C_{2-12}$ alkyl groups, as defined above, having at least one carbon-carbon triple bond, such as —CH$_2$C≡CH.

The term "alkylenyl", as used herein, unless otherwise indicated, includes $C_{1-12}$ saturated divalent hydrocarbon radicals having straight or branched moieties.

The term "cryptand" as used herein mean a bi- and polycyclic polyazo-polyether multi-dentate ligand, where three-coordinate nitrogen atoms provide the vertices of a three-dimensional structure.

The term "thiacryptand" as used herein mean a cryptand with at least one oxygen atom replaced by a sulfur atom.

The term "carboxylated" as used herein means that a chemical moiety is substituted with CO$_2$H (or CO$_2^-$).

The term "subject" refers to a human or animal, including all mammals such as primates (particularly higher primates), sheep, dog, rodents (e.g., mouse or rat), guinea pig, goat, pig, cat, rabbit, and cow.

The term "standard electrode potential" means the electrical potential (i.e., the voltage developed) of a reversible electrode at standard state in which solutes are at an effective concentration of 1 mol/liter, the activity for each pure solid, pure liquid, or for water (solvent) is 1, the pressure of each gaseous reagent is 1 atm., and the temperature is 25° C. Standard electrode potentials are reduction potentials. E° is the standard electrode potential while E°′ is the standard reduction potential at pH 7.

In an embodiment, a method of magnetic resonance imaging a target tissue in a subject is provided. The method includes a step of administering a first Eu$^{2+}$-containing complex to the subject. The first Eu$^{2+}$-containing complex has a reduction potential (e.g., E° or E°′) that is more negative than a reduction potential (e.g., E° or E°′ respectively) for a selected compound present in the target tissue. In particular, the first Eu$^{2+}$-containing complex has a reduction potential (e.g., E° or E°′) that is at least 0.01 volts less (i.e., more negative) than the reduction potential (e.g., E° or E°′ respectively) for the selected compound. In a refinement, the first Eu$^{2+}$-containing complex has a reduction potential (e.g., E° or E°′) that is at least 0.5 volts less (i.e., more negative) than the reduction potential (e.g., E° or E°′ respectively) for the selected compound. In another refinement, the first Eu$^{2+}$-containing complex has a reduction potential (e.g., E° or E°′) that is at least, in increasing order of preference, 0.01 volts, 0.02 volts, 0.03 volts, 0.5 volts, 0.6 volts, or 0.8 volts less (i.e., more negative) than the reduction potential (e.g., $E°$ or $E°'$ respectively) for the selected compound. In a further refinement, the first $Eu^{2+}$-containing complex has a reduction potential (e.g., $E°$ or $E°'$) that is at most, in increasing order of preference, 2 volts, 1 volts, 0.9 volts, 0.8 volts, 0.7 volts, or 0.5 volts less (i.e., more negative) than the reduction potential (e.g., $E°$ or $E°'$ respectively) for the selected compound. A first set of images of the target tissue in the subject is taken by magnetic resonance imaging and in particular, by $T_1$-weighted magnetic resonance imaging. In a refinement, the first set of images is used determine distribution of the selected compound in the target tissue. In a variation, a second $Eu^{2+}$-containing complex is administered to the subject. The second $Eu^{2+}$-containing complex has a reduction potential ($E°$ or $E°'$) is more positive than a reduction potential for the selected compound. In particular, the second $Eu^{2+}$-containing complex has a reduction potential (e.g., $E°$ or $E°'$) that is at least 0.01 volts greater (i.e., more positive) than the reduction potential (e.g., $E°$ or $E°'$ respectively) for the selected compound. In a refinement, the second $Eu^{2+}$-containing complex has a reduction potential (e.g., $E°$ or $E°'$) that is at least 0.5 volts greater (i.e., more positive) than the reduction potential (e.g., $E°$ or $E°'$ respectively) for the selected compound. In another refinement, the second $Eu^{2+}$-containing complex has a reduction potential (e.g., $E°$ or $E°'$) that is at least, in increasing order of preference, 0.01 volts, 0.02 volts, 0.03 volts, 0.5 volts, 0.6 volts, or 0.8 volts greater (i.e., more positive) than the reduction potential (e.g., $E°$ or $E°'$ respectively) for the selected compound. In a further refinement, the second $Eu^{2+}$-containing complex has a reduction potential (e.g., $E°$ or $E°'$) that is at most, in increasing order of preference, 2 volts, 1 volts, 0.9 volts, 0.8 volts, 0.7 volts, or 0.5 volts greater (i.e., more positive) than the reduction potential (e.g., $E°$ or $E°'$ respectively) for the selected compound. A second set of images of the target tissue in the subject is taken by magnetic resonance imaging and in particular, by $T_1$-weighted magnetic resonance imaging. Advantageously, the first set of images and the second set of images are compared to identify regions that possess different concentrations of the selected compound. In the first imaging experiment, the first $Eu^{2+}$-containing complex has a reduction potential that is more negative than the reduction potential for a selected compound resulting in it being oxidized by the selected compound such that the $Eu^{2+}$ is converted to $Eu^{3+}$. This causes a reduction or loss of the T1-weighted contrast enhancement in the magnetic resonance image (i.e., appears darker). In the second experiment, the reduction potential of the second $Eu^{2+}$-containing complex is higher than the selected compound resulting in lower or no conversion to $Eu^{3+}$. When the images between the first and second experiments are compared, regions having the selected compound will be darker in the first experiment when compared to the second experiment.

It should be appreciated that the first $Eu^{2+}$-containing complex and the second $Eu^{2+}$-containing complex have reductions potential bracketing the reduction potential of the compound. The selected compound is a compound that is known to be present in a tissue of interest for magnetic resonance imaging. Table 1 set forth in FIG. 1 provides reduction potentials for several compounds of biological interest and their related redox reaction. In a variation, the first $Eu^{2+}$-containing complex and the second $Eu^{2+}$-containing complex are administered in separate imaging experiments in the vicinity of a tissue of interest. For example, these complexes can be injected into the tissue of interest or within 1 to 10 cm of the tissue of interest.

The method of the present invention advantageously takes advantage of the tuneability of the reductions potential for $Eu^{2+}$-containing complexes. Typically, the reduction potential of a given $Eu^{2+}$-containing complex depends on the ligands in the complex. In a variation, first europium metal complex and second $Eu^{2+}$-containing complex independently include a europium metal ion ($Eu^{2+}$) and a multi-dentate ligand selected from the group consisting of cryptands and thiacryptands and if necessary counter-ions to maintain charge neutrality (i.e., balances a charge of the europium metal ion and the multi-dentate ligand). Characteristically, the europium metal ion is switchable between a 2+ and 3+ oxidation state. Suitable europium metal complexes and ligands are set forth in International Patent Application No. PCT/US14/23283 filed on Mar. 11, 2014; the entire disclosure of this patent application is hereby incorporated by reference. For example, the multi-dentate ligand can generally described by formula I and the first and/or second $Eu^{2+}$-containing complex by formula II:

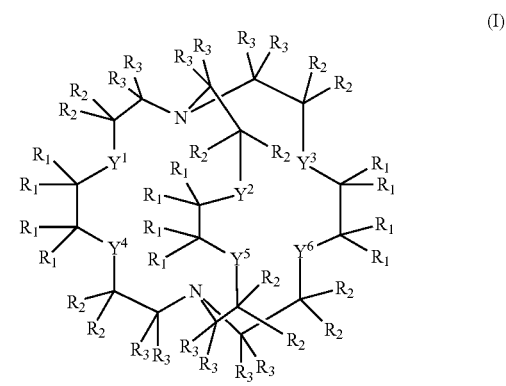

wherein:
Y¹, Y², Y³, Y⁴, Y⁵, and Y⁶ are each independently O or S;
R₁, R₂, R₃ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by combining R₁ on adjacent carbon atoms or R₂ and R₃ on adjacent carbon atoms, =O by combining R₁, R₂, or R₃ on the same carbon atom, =S by combining R₁, R₂, or R₃ on the same carbon atom, or =NR by combining R₁, R₂, or R₃ on the same carbon atom; and R is H or $C_{1-12}$ alkyl. $X^-$ is a counterion such as halide (i.e, $Cl^-$, $Br^-$, $I^-$, etc), mesylate, tosylate and the like. It should be appreciated that in accordance with this terminology the $R_1$ may be different from each other, the $R_2$ may be different from each other, and the $R_3$ may be different from each other. In a refinement, $R_1$ on adjacent carbon atoms or $R_2$ and $R_3$ on adjacent carbon atoms form a phenyl group. In another refinement, $R_1$, $R_2$, or $R_3$ are each independently H, phenyl, or biphenyl. In some refinements, $R_2$ and $R_3$ are hydrogen and one of the $R_1$ is not hydrogen. In other refinements, $R_2$ and $R_3$ are hydrogen and two of the $R_1$ are not hydrogen. Examples of cryptands and thiacryptands and europium complexes including these moieties that useful in the compositions of the present invention are set forth in U.S. Pat. Pub. No. 20130078189 and in J. Garcia et al., *Physical Properties of $Eu^{2+}$-Containing Cryptates as Contrast Agents for Ultrahigh-Field Magnetic Resonance Imaging*, Eur. J. Inorg. Chem. 2012, 2135-2140; the entire disclosures of which are hereby incorporated by reference in their entirety.

The Examples below are included to demonstrate preferred embodiments of the invention. It should be appreciated by those of skill in the art that the techniques disclosed in the Examples represent techniques and compositions discovered by the inventors to function well in the practice of embodiments disclosed herein, and thus can be considered to constitute preferred modes for its practice. However, those of skill in the art should, in light of the present disclosure, appreciate that many changes can be made in the specific embodiments which are disclosed and obtain a like or similar result without departing from the spirit and scope of embodiments disclosed herein.

Figure 2A:
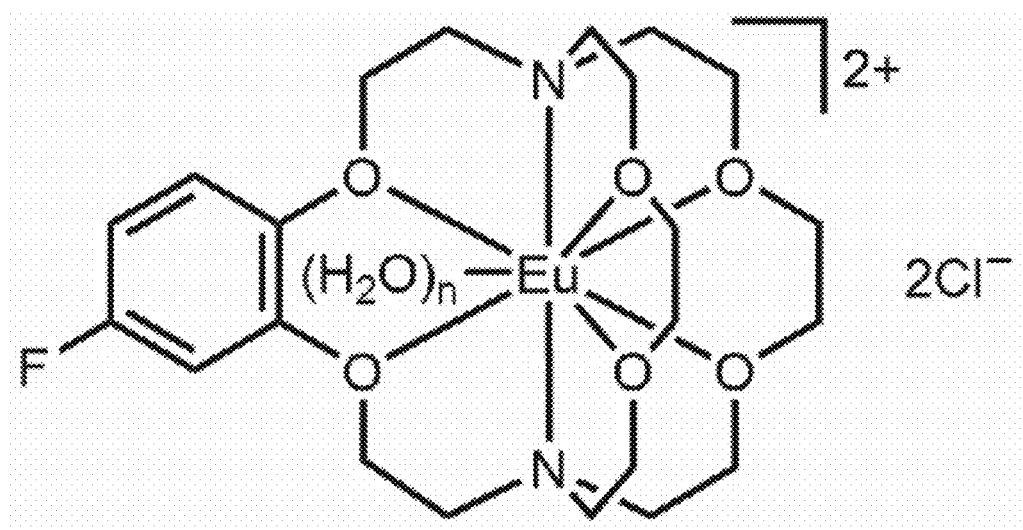
FIGS. 2A and 2B. (A) Proposed solution-phase structure of $Eu^{II}$-222Fb with non-coordinated chloride counteranions and one or two coordinated water molecules (n=1 or 2). (B) X-ray crystal structure of $Eu^{II}$-222Fb with a coordinated chloride ion (hydrogen atoms and the outer sphere chloride counteranion are not shown for clarity). R-factor=0.0248. Resolution=0.59 Å. Thermal ellipsoids are drawn at the 50% probability level.

In vivo imaging with $Eu^{II}$-222Fb (222Fb=5,6-(4-fluorobenzo)-4,7,13,16,21,24-hexaoxa-1,10-diazabicyclo[8.8.8] hexacos-5-ene, FIG. 2) was performed because this complex has a relatively positive oxidation peak potential (0.366 V vs normal hydrogen electrode). More positive potentials favor the +2 oxidation state that is desirable for imaging. However, $Eu^{II}$-222Fb is prone to oxidation by molecular oxygen, and the $Eu^{II}$ ion in this cryptate was expected to be oxidized to $Eu^{III}$ in tissues containing appreciable levels of molecular oxygen or other strong oxidants. In healthy tissue, intracellular environments tend to be reducing while extracellular environments tend to be oxidizing, but in necrotic tissue, dead cells leach components of the cytosol into extracellular space to create a relatively reducing environment. It is hypothesized that the reducing environment of necrotic tissue would prevent oxidation of $Eu^{II}$-222Fb and, consequently, contrast enhancement would be observed in necrotic tissue in the presence of $Eu^{II}$-222Fb. Before imaging in vivo, we characterized $Eu^{II}$-222Fb using solid- and solution-phase techniques.

The X-ray crystal structure of $Eu^{II}$-222Fb (FIG. 2B) features a nine-coordinate metal center in an eclipsed hulahoop geometry. Eight coordination sites are occupied by six oxygen and two nitrogen atoms of 222Fb and the ninth site is occupied by a coordinated chloride counteranion. Interestingly, this nine-coordinate geometry is different than the ten-coordinate geometry of a $Sr^{II}$-containing [2.2.2] cryptate (without the fluorobenzo group) that contains a coordinated water molecule and coordinated trifluoromethanesulfonate anion. This difference is noteworthy because $Sr^{II}$ and $Eu^{II}$ have similar ionic radii, and $Sr^{II}$ is often used as a diamagnetic analog for $Eu^{II}$. Because coordination environment is a key parameter in the characterization of contrast agents for MRI, we interrogated the coordination environment of $Eu^{II}$-222Fb in solution.

To test whether chloride remained coordinated in solution, we measured the molar conductivity of $Eu^{II}$-222Fb in water. The molar conductivity was 211±1 S $cm^2$ $mol^{-1}$, which is consistent with compounds exhibiting a 2:1 dissociation in water. This observation indicates that, on average, no chlorides are coordinated to $Eu^{II}$ in solution. However, because molar conductivity is a colligative property, it does not provide further information regarding the coordination environment of $Eu^{II}$-222Fb in solution.

Figure 2B:
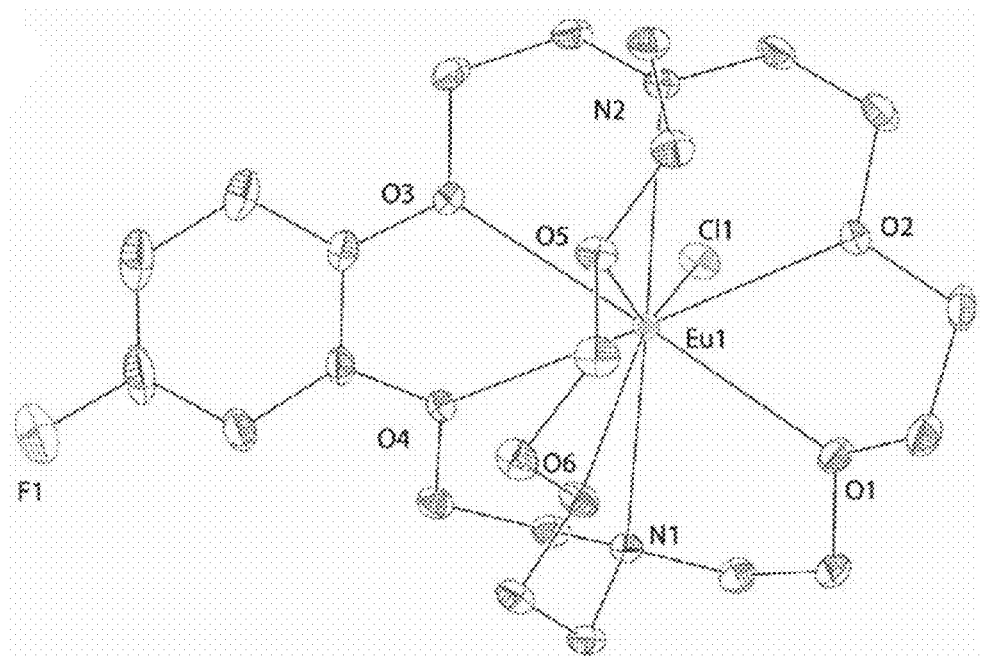

To further characterize the coordination environment of $Eu^{II}$-222Fb in solution, we used variable-temperature $^{17}O$-NMR spectroscopy to investigate water coordination. Using 1% enriched $H_2^{17}O$ in phosphate-buffered saline, we were able to observe a paramagnetic broadening of the $^{17}O$-NMR signal upon addition of $Eu^{II}$-222Fb. The line broadening is consistent with the presence of inner sphere water. This observation coupled with a 2:1 dissociation suggests that in solution $Eu^{II}$-222Fb is present either as a nine-coordinate species with chloride displaced by a water molecule or as a ten-coordinate species, based on the ability of $Eu^{II}$ to adopt ten-coordinate geometries, with two coordinated water molecules after chloride dissociation (FIG. 2B). It is unlikely that more than two water molecules coordinate because 222Fb occupies eight coordination sites and because to the best of our knowledge, no eleven-coordinate molecular $Eu^{II}$-containing complexes have been reported. After studying the coordination environment of $Eu^{II}$-222Fb, we turned to in vitro MRI to characterize its ability to influence contrast.

To characterize the ability of $Eu^{II}$-222Fb to provide contrast enhancement, we measured the relaxivity of $Eu^{II}$-222Fb in phosphate-buffered saline using $T_1$-weighted MRI. The relaxivity (24° C., 7 T) of $Eu^{II}$-222Fb in phosphate-buffered saline was 6.5±0.3 $mM^{-1}$ $s^{-1}$. Our measured relaxivity in phosphate-buffered saline is in agreement with other $Eu^{II}$-containing cryptates.[2b] Additionally, phosphate can bind lanthanide ions in a bidentate manner to displace two water molecules when the metal ion contains two adjacent coordinated water molecules.[9]

Figure 3A:
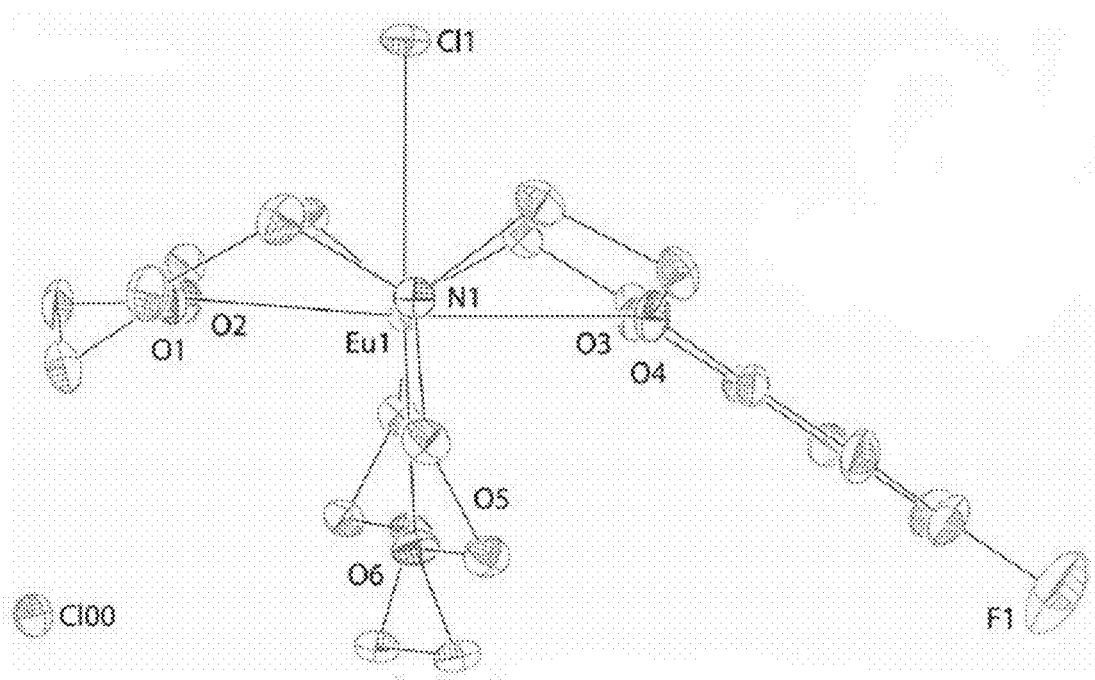
FIGS. 3A and 3B. (A) X-ray crystal structure (viewed along the N—Eu—N axis) of $Eu^{II}$-222Fb (hydrogen atoms are not shown for clarity) alongside a cartoon representation of the solid-phase geometry in the same orientation as the crystal structure. Outer sphere chloride, C100, related by symmetry is included in the image. (B) Cartoon representation of the proposed solution-phase geometry of $Eu^{II}$-222Fb with one or two coordinated water molecules viewed along the N—Eu—N axis. The blue and teal spheres in the cartoons represent nitrogen and europium, respectively, and the bold lines represent the cryptands. R-factor=0.0248. Resolution=0.59 Å. Thermal ellipsoids are drawn at the 50% probability level.
Figure 3B:
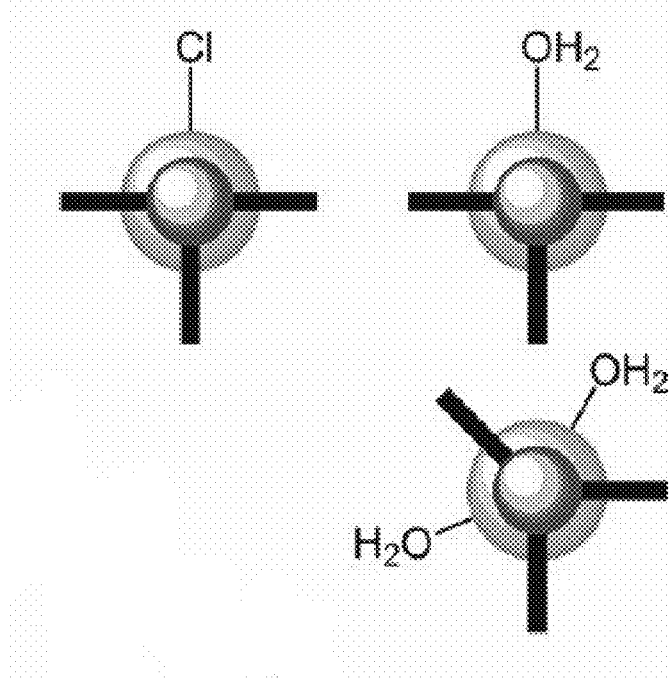

Nonadjacent water would be consistent with water molecules replacing the two chloride ions (FIG. 3B). While not coordinated, the outer sphere chloride is 5.383 Å from $Eu^{II}$ (the coordinated chloride is 2.793 Å from $Eu^{II}$), and if both chloride ions are replaced by water molecules, a closer approach could be envisioned due to the smaller size of oxygen relative to chloride. Accordingly, our measured $^{17}O$ line broadening, crystal structure, and relaxivity suggest that if two water molecules are coordinated to $Eu^{II}$-222Fb in solution, that they are likely not adjacent to each other.

To test whether $Eu^{II}$-222Fb would enhance contrast in necrotic tissue, we performed $T_1$-weighted MRI before and after intratumoral injection of $Eu^{II}$-222Fb (50 μL, 19.4 mM) into a 4T1 mammary carcinoma. The 4T1 carcinoma model is an aggressive tumor that typically develops a necrotic core,[10] and imaging was performed when tumors reached approximately 700-1000 mg to maximize the probability of necrosis. Images were acquired before and at 3, 20, and 120 min after intratumoral injection (FIG. 3A-D). Positive contrast enhancement was observed for the entirety of the 120 min experiment, but the location of positive contrast enhancement changed over time. Specifically, heterogeneous positive contrast enhancement was observed along nearly the entire length of the tumor immediately post injection, but was only observed in a localized core of the tumor after 120 min. These observations demonstrate that $Eu^{II}$ persists within a tumor for at least 120 min, and we observed this duration of positive contrast enhancement in all seven of our attempted imaging experiments with independently injected tumors. The presence of contrast enhancement is consistent with the persistence of the +2 oxidation state of europium in the core of the tumor, and the reduced oxidation state is suggestive of a lack of oxygen.

Figure 4A:
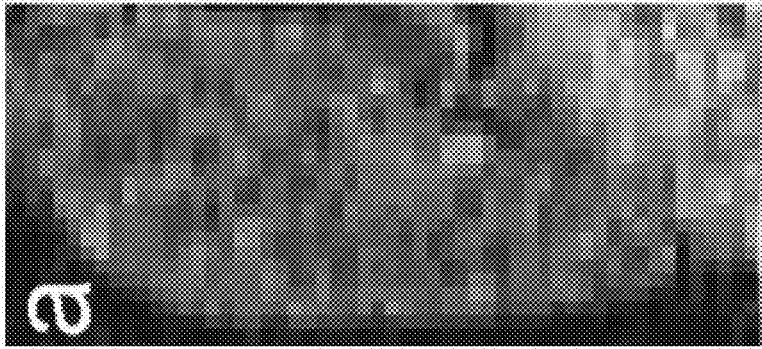
FIGS. 4A-G. $T_1$-weighted in vivo sagittal plane images of a 4T1 tumor injected with $Eu^{II}$-222Fb (A) pre-injection; (B) 3 min, (C) 20 min, and (D) 120 min post-intratumoral injection; (E) difference between the 120 min and pre-injection images (image d minus image a) colored using the ImageJ green lookup table; (F) hematoxylin- and eosin-stained slice of tumor imaged in a-e; and (G) sum of images e and f. All images are on the same scale. Imaging parameters included an echo time of 1.5 ms, repetition time of 11 ms, flip angle of 40°, field of view of 30 mm×90 mm, and an in-plane resolution of 0.352 mm×0.352 mm.
Figure 4B:
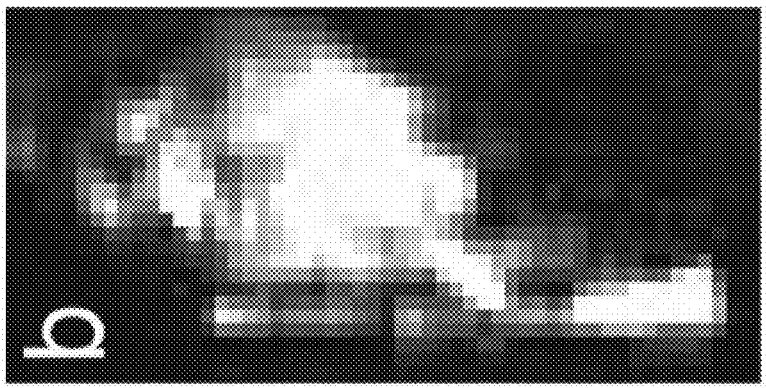
Figure 4C:
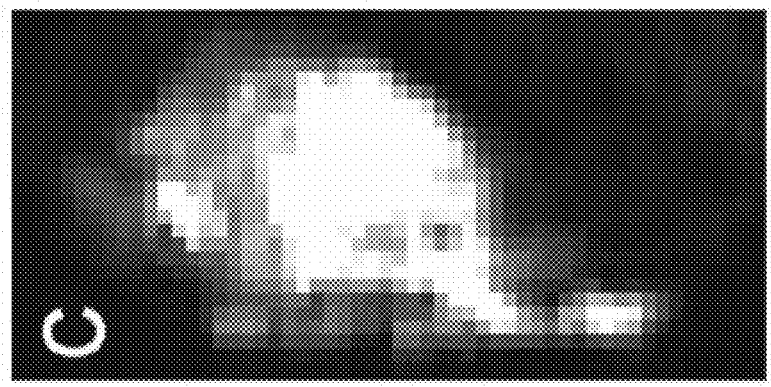
Figure 4D:
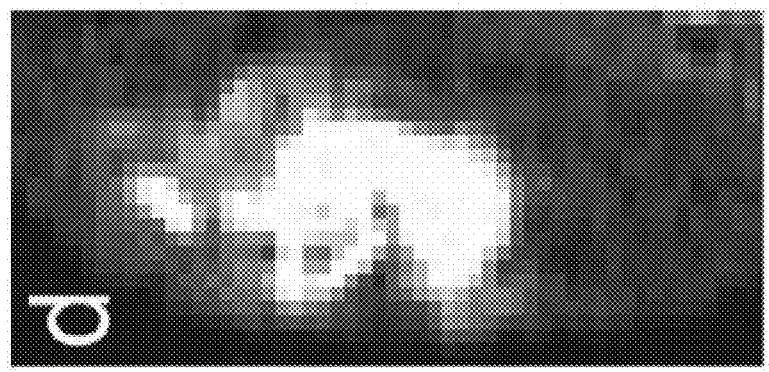
Figure 4G:
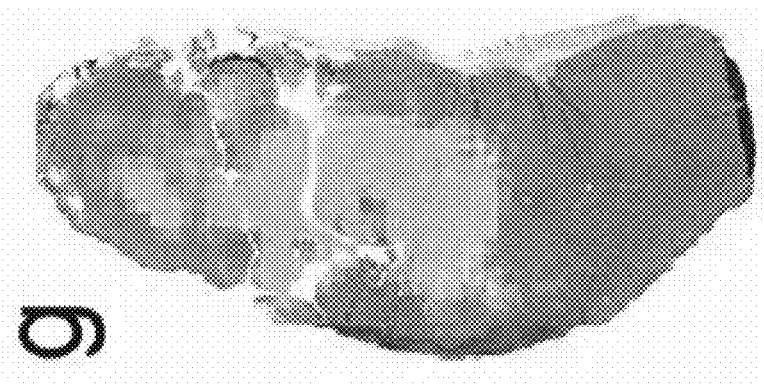
Figure 4F:
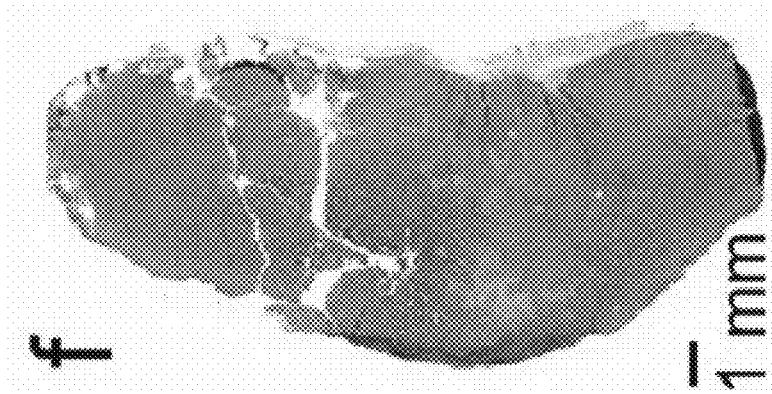
Figure 4E:
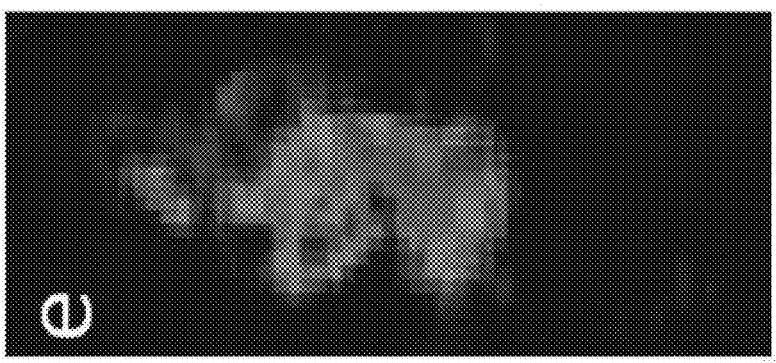

To verify the presence of necrotic tissue in the tumor, we sacrificed the mouse directly after the 120 min post-injection image and performed histological staining. The tumor was removed in whole, fixed in formalin, mounted in paraffin, and cut to a thickness of 5 μm before being stained with hematoxylin and eosin (FIG. 4F). Hematoxylin is a dye that stains nuclei, and eosin stains elements of the cytoplasm as a counterstain to differentiate areas that are nuclei-abundant (blue) from those that are nuclei-deficient (pink). Areas associated with necrosis are expected to stain pink to a greater extent than non-necrotic areas because of the lack of cells and their corresponding nuclei in necrotic regions. The stained slice revealed nuclei-deficient regions consistent with necrosis that were particularly pronounced in the mid-to-upper half of the tumor. The leftmost region of the slice stained pink from the presence of tumor ulceration through the mouse epidermis. Consistent with staining, the majority of positive contrast enhancement observed 120 min post-injection was in the mid-to-upper half of the tumor, suggesting that $Eu^{II}$-222Fb provided positive contrast enhancement in the necrotic core of the tumor (FIG. 4 G). No contrast enhancement was observed in the leftmost region of the tumor likely because of direct contact between tumor ulceration and oxygen in the air. It is worth reiterating that we used an intratumoral injection, which may have placed a bolus in the tumor core and the lack of oxygen allowed $Eu^{II}$ to persist.

To better understand the potential mechanism of differentiation, we performed an intratumoral injection of $Eu^{II}$-222Fb (50 μL, 6.9 mM) and monitored contrast enhancement over the course of 3 h before sacrificing the mouse and removing the injected tumor for analysis of Eu content by inductively coupled plasma mass spectrometry. At 3 h post-injection, we observed a decrease in positive contrast enhancement (~85%) in the tumor relative to the initial image and a decrease of in the Eu content (~80%) in the tumor relative to the injected dose. These close values suggest clearance of $Eu^{II}$-222Fb played a major role in the loss of positive contrast enhancement. Clearance was not directly observed in $T_1$-weighted MRI because $Eu^{II}$-222Fb likely oxidized in tissues or fluids of relatively higher oxygen content, and the product of oxidation, does not produce positive contrast enhancement. Furthermore, when $Gd^{III}$-1,4,7,10-tetraazacyclododecane-1,4,7,10-tetraacetate (50 μL, 20.5 mM) was injected into a tumor in a separate experiment, the bladder of the mouse was bright with contrast within minutes of the injection. We observed this phenomenon in two independently injected tumors. This non-redox-active control indicates that the concentration of $Eu^{II}$ injected should be enough to visualize in the bladder if clearance occurred without oxidation. The evidence of clearance based on Eu content and the lack of contrast enhancement observed outside of the tumor demonstrates the lack of background enhancement possible with $Eu^{II}$-based imaging agents in redox-active environments. While the connection between positive contrast enhancement and necrotic tissue is intriguing, more detailed experiments are required to evaluate the nature of $Eu^{II}$-222Fb clearance over time. Regardless of the mechanism of differentiation, our in vivo imaging data demonstrate the first reported use $Eu^{II}$ for in vivo contrast-enhanced MRI.

To investigate the in vitro stability of $Eu^{II}$-222Fb with respect to oxygen exposure, we measured $T_1$ (37° C., 1.4 T) of $Eu^{II}$-222Fb in phosphate-buffered saline to monitor the oxidation of $Eu^{II}$ as a function of air exposure while stirring. Under an atmosphere of $N_2$ ($pO_2 \approx 0$ mmHg), $Eu^{II}$-222Fb remained in the +2 oxidation for at least 118 d. However, upon stirring in open air ($pO_2 \approx 160$ mmHg), the observed $T_1$ enhancement was completely lost within 5 min. This rapid oxidation with elevated oxygen exposure suggests that $Eu^{II}$-222Fb is oxidized upon clearance from the oxygen-deficient 4T1 necrotic core ($pO_2 \leq 10$ mmHg)[12,13] into relatively oxygenated vasculature ($pO_2 \approx 40$-100 mmHg).[14] Collectively, the persistence of the +2 oxidation state over a 120 min period, the correlation between necrotic tissue and contrast enhancement, the lack of positive contrast enhancement in organs associated with clearance (bladder, liver, or kidneys), and the rapid oxidation observed in elevated air exposure suggest that $Eu^{II}$-222Fb persists in the poorly oxygenated necrotic core of the tumors and oxidizes elsewhere.

In conclusion, we report solid- and solution-phase characterization of $Eu^{II}$-222Fb that is nine-coordinate in the solid state and nine- or ten-coordinate in solution. Additionally, we report the first in vivo contrast-enhanced MRI with a $Eu^{II}$-based contrast agent, and efforts in our laboratory to understand the behavior of $Eu^{II}$-222Fb in vivo are underway. We expect that the ability to differentiate necrotic from non-necrotic tissue in vivo coupled with the tunable oxidation potential of $Eu^{II}$ will enable bracketing of tissue redox environments associated with both hypoxic and hyperoxic tissues relevant to the study of many diseases.

Experimental Procedures

Commercially available chemicals were of reagent-grade purity or better and were used without further purification unless otherwise noted. 10× Phosphate-buffered saline was purchased from Fisher BioReagents. Water was purified using a PURELAB Ultra Mk2 water purification system (ELGA) and degassed prior to use. Triethylamine was distilled from $CaH_2$.

Flash chromatography was performed using silica gel 60, 230-400 mesh (EMD Chemicals). Analytical thin-layer chromatography (TLC) was performed on ASTM TLC plates pre-coated with silica gel 60 $F_{254}$ (250 μm thickness). TLC visualization was achieved using UV irradiation (254 nm) followed by charring with potassium permanganate stain (3 g $KMnO_4$, 20 g $K_2CO_3$, 5 mL 5% w/v aqueous NaOH, 300 mL $H_2O$).

$^1H$- and $^{13}C$-NMR spectra were obtained using a Varian MR-400 (400 MHz $^1H$, 101 MHz $^{13}C$) spectrometer. $^{19}F$-NMR spectra were obtained using a Mercury 400 (376 MHz $^{19}F$) spectrometer. Chemical shifts are reported relative to residual solvent signals unless otherwise noted ($CDCl_3$: $^1H$: δ 7.27, $^{13}C$: δ 77.23; $(CD_3)_2SO$: $^1H$: δ 2.50, $^{13}C$: δ 39.52; $CD_3CN$: $^1H$: δ 1.94, $^{13}C$: δ 118.26; $CFCl_3$ (internal standard): $^{19}F$: δ 0.00). NMR data are assumed to be first order, and the apparent multiplicity is reported as "s"=singlet, "d"=doublet, "dd"=doublet of doublets, "ddd"=doublet of doublet of doublets, "t"=triplet, "td"=triplet of doublets, "m"=multiplet, or "brs"=broad singlet. Italicized elements are those that are responsible for the shifts. Correlation spectroscopy (COSY), distortionless enhancement by polarization transfer (DEPT), and heteronuclear multiple quantum coherence (HMQC) spectra were used to assign spectral peaks. High-resolution electrospray ionization mass spectra (HRESIMS) were obtained on a Waters LCT premier time-of-flight high-resolution mass spectrometer.

Molar conductivity was calculated from three independently prepared solutions of Eu$^{II}$-222Fb (1.00 mM, 5.00 mL) measured in water under an atmosphere of $N_2$ and ambient temperature using an Omega CDH 280 portable conductivity meter that was calibrated with aqueous KCl (0.01 M, 1.413 mS cm$^{-1}$). Results are reported as mean±standard error.

Tumor digestion was accomplished by adding the whole tumor to a solution of nitric acid (70%, 2 mL) in water (5 mL) in a 25.0 mL volumetric flask. The mixture was heated at 95° C. for 48 h with vigorous stirring to produce a clear, yellow solution. The solution was diluted to 25.0 mL after the removal of the stir bar, and filtered through a 0.2 μm hydrophilic filter. The filtrate was diluted (1:10) for analysis by inductively coupled plasma mass spectrometry (ICP-MS).

ICP-MS measurements were acquired on an Agilent Technologies 7700 series ICP-MS instrument at the Lumigen Instrument Center in the Department of Chemistry at Wayne State University. All dilutions were performed with aqueous 2% $HNO_3$, which was also used for blank samples during calibration. The calibration curve was created using the $^{153}$Eu isotope ion count for a 1-200 ppb concentration range (diluted from Fluka ICP standard solution, $Eu_2O_3$ in aqueous 2% $HNO_3$, 1000 mg Eu/L). All samples were diluted to fall within this range.

Synthetic Procedures and Characterization

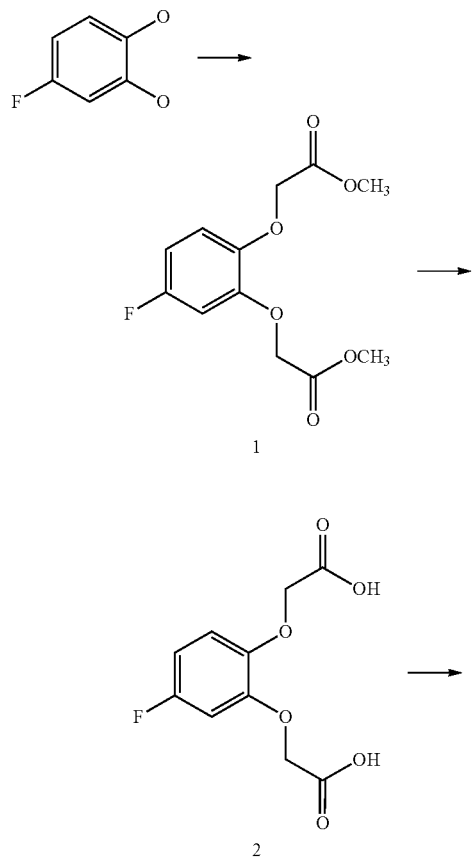

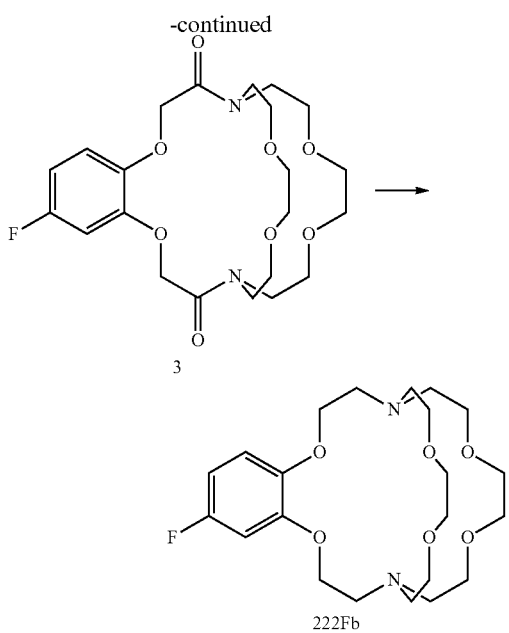

Dimethyl 2,2'-((4-fluoro-1,2-phenylene)bis(oxy))diacetate (1)

A mixture of 4-fluorobenzene-1,2-diol (0.501 g, 3.91 mmol, 1 equiv), acetone (20 mL), potassium carbonate (2.55 g, 18.5 mmol, 4.7 equiv), and methylbromoacetate (2.11 mL, 22.3 mmol, 5.7 equiv) was heated at reflux for 2 h, cooled to ambient temperature, and filtered through a fritted funnel (medium). Solvent was removed from the filtrate under reduced pressure to afford a pale yellow oil. The oil was dissolved in ethyl acetate (15 mL) and washed with water (3×10 mL). The organic layer was dried over anhydrous magnesium sulfate before solvent was removed under reduced pressure to yield 0.986 g (92%) of 1 as a pale yellow oil. $^1$H NMR (400 MHz, CDCl$_3$): δ=3.77-3.82 (m, 6H; CH$_3$), 4.68-4.72 (m, 4H; CH$_2$), 6.59-6.67 (m, 2H; FCCH), 6.90 ppm (dd, $^3$J (H, H)=8.8 Hz, $^4$J (H, F)=5.4 Hz, 1H; OCCHCH); $^{13}$C NMR (101 MHz, CDCl$_3$): δ=52.4 (CH$_3$), 52.5 (CH$_3$), 66.5 (CH$_2$), 67.7 (CH$_2$), 103.4 (d, $^2$J (C, F)=28.2 Hz, FCCH), 108.3 (d, $^2$J (C, F)=21.2 Hz, FCCH), 117.5 (d, $^3$J (C, F)=10.0 Hz, OCCHCH), 144.3 (d, $^4$J (C, F)=3.0 Hz), 149.1 (d, $^3$J (C, F)=10.5 Hz), 158.3 (d, $^1$J (C, F)=241.8 Hz, CF), 169.1, 169.7 ppm; $^{19}$F NMR (376 MHz, CDCl$_3$, CFCl$_3$): δ=−118.7 to ~118.6 ppm (m, F); HRESIMS (m/z): [M+Na]$^+$ calcd for C$_{12}$H$_{13}$O$_6$FNa, 295.0594; found, 295.0594.

2,2'-((4-Fluoro-1,2-phenylene)bis(oxy))diacetic Acid (2)

To a mixture of 1 (0.874 g, 3.21 mmol, 1 equiv) and water (25 mL) was added DOWEX (200 mesh, 50 W×8, hydrogen form) resin (0.456 g). The mixture was heated at reflux without stirring for 60 h at which point it was filtered while hot through Whatman number 1 filter paper. Solvent was removed under reduced pressure to afford 0.742 g (96%) of 2 as an off-white solid. $^1$H NMR (400 MHz, (CD$_3$)$_2$SO): δ=4.65 (s, 2H; CH$_2$), 4.74 (s, 2H; CH$_2$), 6.70 (td, $^3$J (H, F)=8.6 Hz, $^4$J (H, H)=2.9 Hz, 1H; FCCHCH), 6.84 (dd, $^3$J (H, F)=10.3 Hz, $^4$J (H, H)=2.9 Hz, 1H; FCCHCO), 6.91 (dd, $^3J$ (H, H)=8.8 Hz, $^4J$ (H, F)=5.4 Hz, 1H; OCCHCH), 13.00 ppm (brs, 2H; OH); $^{13}C$ NMR (101 MHz, (CD$_3$)$_2$SO): δ=65.1 (CH$_2$), 65.8 (CH$_2$), 102.1 (d, $^2J$ (C, F)=27.9 Hz, FCCHCO), 106.4 (d, $^2J$ (C, F)=24.4 Hz, FCCHCH), 115.2 (d, $^3J$ (C, F)=10.5 Hz, OCCHCH), 143.8 (d, $^4J$ (C, F)=3.0 Hz), 148.4 (d, $^3J$ (C, F)=10.3 Hz), 156.8 (d, $^1J$ (C, F)=237.4 Hz, CF), 169.9, 170.3 ppm; $^{19}F$ NMR (376 MHz, (CD$_3$)$_2$SO, CFCl$_3$): δ=−119.9 to ~119.8 ppm (m, F); HRESIMS (m/z): [M+Na]$^+$ calcd for C$_{10}$H$_9$O$_6$FNa, 267.0281; found, 267.0278.

Diamide (3)

To 2 (0.571 g, 2.34 mmol, 1 equiv) was added thionyl chloride (10 mL, 0.14 mol, 60 equiv) under an atmosphere of Ar. The mixture was heated at reflux for 2 h (the mixture turned to a clear, yellow solution during this time) before excess thionyl chloride was removed under reduced pressure to afford a dark yellow oil. The dark yellow oil was dissolved in anhydrous toluene (50 mL). A separate solution of 4,13-diaza-18-crown-6-ether (0.613 g, 2.34 mmol, 1 equiv), triethylamine (3.0 mL, 22 mmol, 9.4 equiv), and chloroform (7 mL) in anhydrous toluene (40 mL) was prepared. Both solutions were simultaneously added dropwise over 1 h to a flask containing anhydrous toluene (500 mL) at 0° C. under an atmosphere of Ar. After the additions, the reaction mixture was allowed to warm to ambient temperature and was stirred for 5 h before solvent was removed under reduced pressure. Purification was performed using silica gel chromatography (8:1 dichloromethane/methanol) to yield 0.646 g (59%) of 3 as a white solid. $^1H$ NMR (400 MHz, CD$_3$CN): δ=2.69-2.82 (m, 2H; CH$_2$), 3.20-3.33 (m, 2H; CH$_2$), 3.38-3.77 (m, 18H; CH$_2$), 4.13 (ddd, $^2J$ (H, H)=14.4 Hz, $^3J$ (H, H)=4.8 Hz, $^3J$ (H, H)=2.8 Hz, 1H; CH$_2$CH$_2$), 4.23 (ddd, $^2J$ (H, H)=14.2 Hz, $^3J$ (H, H)=6.2 Hz, $^3J$ (H, H)=2.9 Hz, 1H; CH$_2$), 4.64 (d, $^2J$ (H, H)=14.7 Hz, 1H; CH$_2$CH$_2$), 4.75 (d, $^2J$ (H, H)=14.7 Hz, 1H; CH$_2$), 5.27 (d, $^2J$ (H, H)=14.7 Hz, 1H; CH$_2$), 5.40 (d, $^2J$ (H, H)=14.7 Hz, 1H; CH$_2$), 6.60 (td, $^3J$ (H, H, F)=8.6 Hz, $^4J$ (H, H)=2.9 Hz, 1H; FCHCH), 6.75 (dd, $^3J$ (H, F)=10.3 Hz, $^4J$ (H, H)=2.9 Hz, 1H; OCCHCF), 6.93 ppm (dd, $^3J$ (H, H)=8.8 Hz, $^4J$ (H, F)=5.9 Hz, 1H; OCHCH); $^{13}C$ NMR (101 MHz, CD$_3$CN): δ=48.7 (CH$_2$), 49.0 (CH$_2$), 49.1 (CH$_2$), 49.4 (CH$_2$), 67.8 (CH$_2$), 68.9 (CH$_2$), 69.9 (CH$_2$), 70.0 (CH$_2$), 70.2 (CH$_2$), 70.5 (CH$_2$), 71.5 (CH$_2$), 71.6 (CH$_2$), 71.8 (CH$_2$), 71.9 (CH$_2$), 104.3 (d, $^2J$ (C, F)=27.1 Hz, OCCHCF), 107.6 (d, $^2J$ (C, F)=23.2 Hz, FCHCH), 118.7 (d, $^3J$ (C, F)=9.9 Hz, OCHCH), 145.4 (d, $^4J$ (C, F)=3.0 Hz), 150.2 (d, $^3J$ (C, F)=10.7 Hz), 158.5 (d, $^1J$ (C, F)=237.8 Hz, CF), 169.3, 169.6 ppm; $^{19}F$ NMR (376 MHz, CDCl$_3$, CFCl$_3$): δ=−121.0 to −120.9 ppm (m, F); TLC: R$_f$=0.53 (8:1 dichloromethane/methanol); HRESIMS (m/z): [M+Na]$^+$ calcd for C$_{22}$H$_{31}$N$_2$O$_8$FNa, 493.1962; found, 493.1956.

5,6-(4-Fluorobenzo)-4,7,13,16,21,24-hexaoxa-1,10-diazabicyclo[8.8.8]hexacos-5-ene (222Fb)

To 3 (0.549 g, 1.17 mmol, 1 equiv) was added borane tetrahydrofuran complex (1.0 M, 35.0 mL, 35.0 mmol, 30 equiv) under an atmosphere of Ar. The solution was heated at reflux for 23 h before the reaction was allowed to cool to ambient temperature. To the reaction solution was slowly added hydrochloric acid (3.0 M, 50 mL, 15 mmol, 13 equiv) over 10 min, and the resulting white, turbid mixture was heated at reflux for 3 h to form a clear, colorless solution before it was allowed to cool to ambient temperature. The pH of the reaction solution was adjusted to 11 with the addition of concentrated ammonium hydroxide (20 mL) before solvent was removed under reduced pressure to afford a white solid. Purification was achieved using silica gel chromatography (8:1 dichloromethane/methanol) to yield a white oily solid that was dissolved in a concentrated cesium carbonate solution (pH<10) and extracted with chloroform (3×15 mL). The organic layers were combined, dried over anhydrous magnesium sulfate, filtered through a fine glass frit, and solvent was removed under reduced pressure to yield 0.417 g (81%) of 222Fb as a colorless oil. $^1H$ NMR (400 MHz, CDCl$_3$): δ=2.68-2.79 (m, 8H; CH$_2$), 2.90 (t, $^3J$ (H, H)=6.4 Hz, 2H; CH$_2$), 2.95 (t, $^3J$ (H, H)=5.4 Hz, 2H; CH$_2$), 3.51-3.68 (m, 16H; CH$_2$), 4.05-4.13 (m, 4H; CH$_2$), 6.56 (td, $^3J$ (H, H, F)=8.6 Hz, $^4J$ (H, H)=2.9 Hz, 1H; FCCHCH), 6.62 (dd, $^3J$ (H, F)=9.8 Hz, $^4J$ (H, H)=2.9 Hz, 1H; FCCHCO), 6.82 ppm (dd, $^3J$ (H, H)=8.8 Hz, $^4J$ (H, F)=5.4 Hz, 1H; OCHCH); $^{13}C$ NMR (101 MHz, CDCl$_3$): δ=55.1 (CH$_2$), 55.4 (CH$_2$), 56.1 (CH$_2$), 56.4 (CH$_2$), 68.1 (CH$_2$), 69.8 (CH$_2$), 70.2 (CH$_2$), 70.4 (CH$_2$), 70.9 (CH$_2$), 71.2 (CH$_2$), 102.8 (d, $^2J$ (C, F)=26.5 Hz, FCCHCO), 106.6 (d, $^2J$ (C, F)=21.7 Hz, FCCHCH), 117.2 (d, $^3J$ (C, F)=10.8 Hz, OCHCH), 145.4 (d, $^4J$ (C, F)=2.4 Hz), 150.7 (d, $^3J$ (C, F)=10.8 Hz), 158.0 ppm (d, $^1J$ (C, F)=238.3 Hz, CF); $^{19}F$ NMR (376 MHz, CDCl$_3$, CFCl$_3$): δ=−120.2 to −120.0 ppm (m, F); TLC: R$_f$=0.32 (8:1 dichloromethane/methanol); HRESIMS (m/z): [M+Na]$^+$ calcd for C$_{22}$H$_{35}$N$_2$O$_6$FNa, 465.2377; found, 465.2384.

Preparation of Complexes

Contrast agent solutions were prepared by adding aqueous EuCl$_2$ (100.5 μL, 199.1 mM) and aqueous 222Fb (379.5 μL, 52.7 mM) in a 1:1 stoichiometry to 420.0 μL water in a 4 mL glass vial equipped with a magnetic stir bar under an inert atmosphere. The resulting clear, colorless solution was stirred for 1 h before addition of degassed 10× phosphate-buffered saline and water to achieve a solution of Eu$^{II}$-222Fb (approximate concentration of 20 or 10 mM) in phosphate-buffered saline (11.9 mM phosphates, 137 mM sodium chloride, 2.7 mM potassium chloride, pH 7.4). The clear, colorless solution was stirred for 30 min then filtered through a 0.2 μm hydrophilic filter (uncomplexed Eu$^{II}$ precipitates as phosphate salts).[1] Solutions for T$_1$ mapping and $^{17}$O-NMR studies were prepared in the same manner. Eu concentrations after filtration were determined by ICP-MS to be 19.4 and 6.9 mM for Eu$^{II}$-222Fb used for injections; 0.93, 0.64, and 0.32 mM Eu$^{II}$-222Fb used for T$_1$ mapping; and 9.58 mM Eu$^{II}$-222Fb used for $^{17}$O-NMR studies.

X-ray quality crystals of Eu$^{II}$-222FbCl$_2$ were prepared by dissolving EuCl$_2$ (7.2 mg, 0.032 mmol, 1 equiv) and 222Fb (19 mg, 0.043 mmol, 1.3 equiv) in methanol (0.25 mL) under an atmosphere of N$_2$. The resulting clear, yellow solution was stirred for 1 h before the addition of tetrahydrofuran (3.0 mL). Solvent was slowly evaporated to afford pale yellow needle-like crystals.

Animal Models

Studies in animals were carried out with the assistance of the Animal Model and Therapeutics Evaluation Core of the Barbara Ann Karmanos Cancer Institute after approval from the Wayne State University Institutional Animal Care and Use Committee. Methods of protocol design, toxicity evaluation, drug treatment, and use of transplantable tumor model systems have been previously reported.[2,3] A brief description of the methods as they apply to this work is as follows: Female BALB/cAnNCr mice (National Cancer Institute Animal Breeding Program; Charles River) were implanted with the syngeneic murine mammary tumor model 4T1.[4] Tumors were maintained in the mouse strain of origin (BALB/c) and housed in animal facilities accredited by the Association for Assessment and Accreditation of Laboratory Animal Care with 24/7 veterinary oversight of care and husbandry. Animals were pooled, implanted bilaterally subcutaneously with 30-60 mg tumor fragments with a 12 gauge trocar, and imaged when tumors reached approximately 700-1000 mg in size (determined by caliper measurements: tumor mass (mg)≈[tumor length (mm)×tumor width$^2$ (mm$^2$)]/2). All mice were a minimum of 18 g before entering the study and were provided food and water ad libitum.

Magnetic Resonance Imaging

Magnetic resonance imaging (MRI) was performed using a 7 T Bruker Clinscan small animal MRI scanner with a 30 cm bore in the MR Research Facility at Wayne State University. Whole body coronal plane images were acquired using a 3D FLASH sequence with an echo time of 1.5 ms, repetition time of 11 ms, flip angle of 40°, 44 image slices at 0.5 mm thickness, a 30 mm×90 mm field of view, and an in-plane resolution of 0.352 mm×0.352 mm.

Imaging studies were performed with female tumor bearing BALB/cAnNCr mice. Animals were first anesthetized (1.5-2% v/v isoflurane in oxygen) and immobilized on a bed heated by circulating temperature-controlled water (37° C.). Mice were imaged before injections, briefly removed from the magnet (while still stably positioned on the bed), injected, then returned to the magnet imaged immediately to acquire the first time point (3 min) post-injection and imaged again at a subsequent times of 20 and 120 min post-injection. Intratumoral injections were performed using tuberculin syringes (1 mL) fitted with 27 gauge×0.5 in. needles. After all necessary measurements and images were obtained, animals were immediately humanely euthanized. Flank tumors were removed immediately and placed directly into 10% buffered formalin for histology or dissolved nitric acid for analysis of Eu content.

Histology

Fixed tissue paraffin embedding, hematoxylin and eosin staining, paraffin sectioning, and optical microscopy of stained sections were performed at the Biobanking and Correlative Sciences Core of the Barbara Ann Karmanos Cancer Institute.

Figure 5A:
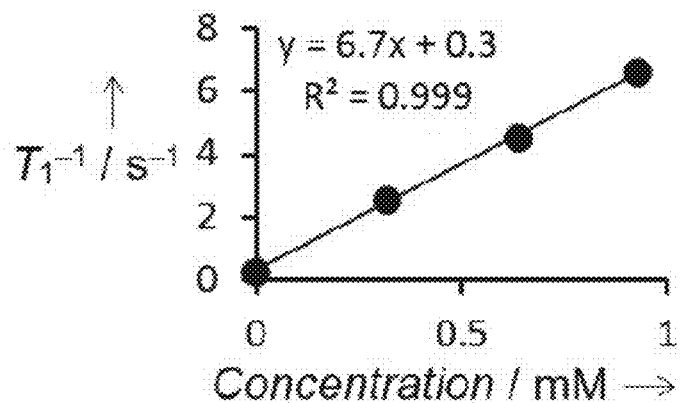
FIGS. 5A-C. Longitudinal relaxation rate vs $Eu^{II}$-222Fb concentration in phosphate-buffered saline.
Figure 5B:
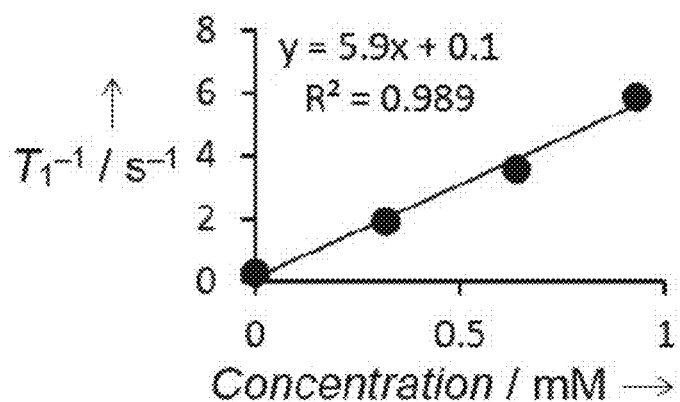
Figure 5C:
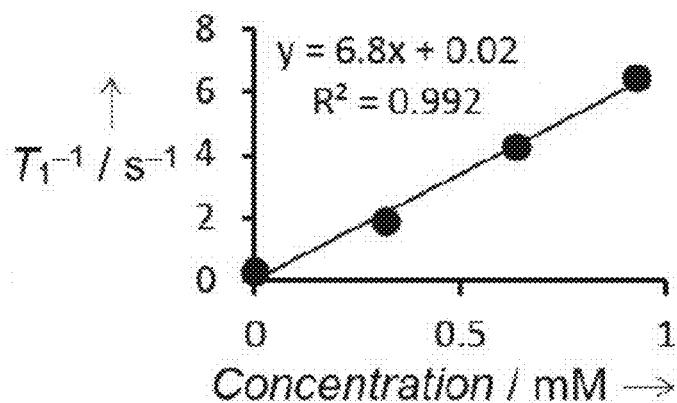

Relaxivity Data $T_1$ maps were acquired using a published procedure for the accurate determination of $T_1$ in the presence of radiofrequency-field inhomogeneities and flip-angle miscalibration.[5] The relaxivity plots were triplicated measurements of independently prepared samples (FIG. 5). The slopes of the relaxivity plots were used to calculate the mean relaxivity plus or minus the standard error of the mean.

$^{17}$O-NMR Spectroscopy Data

Variable-temperature $^{17}$O-NMR measurements of Eu$^{II}$-222Fb (9.58 mM) in phosphate-buffered saline (pH=7.4) and a pH=7.4 blank of phosphate buffered saline were obtained on a Varian-500S (11.7 T) spectrometer. $^{17}$O-enriched water (20% H$_2$$^{17}$O, Cambridge Isotope Laboratories, Inc.) was added to samples to achieve 1% enrichment in $^{17}$O. Line widths at half height were measured at 30, 40, 50, 60, and 70° C. The $^{17}$O-NMR data and fits are presented in Table 2.

TABLE 2

$^{17}$O linewidths for Eu$^{II}$-222Fb and phosphate buffer as a function of temperature.

| Temperature | Linewidth (Hz) | |
|---|---|---|
| (° C.) | Eu$^{II}$-222Fb | phosphate buffer |
| 70 | 45 | 30 |
| 60 | 57 | 35 |

TABLE 2-continued $^{17}$O linewidths for Eu$^{II}$-222Fb and phosphate buffer as a function of temperature.

| Temperature | Linewidth (Hz) | |
|---|---|---|
| (° C.) | Eu$^{II}$-222Fb | phosphate buffer |
| 50 | 77 | 42 |
| 40 | 103 | 53 |
| 30 | 144 | 72 |

Crystallographic Data

Crystal structure analysis was performed on a Bruker APEX-II Kappa geometry diffractometer with Mo radiation and a graphite monochromator using a Bruker charge coupled device based diffractometer equipped with an Oxford Cryostream low-temperature apparatus. The data was measured at a temperature of 100 K. The structure was solved by the direct method using the SHELXS-97 program that is part of APEX II2 and refined by the least squares method, SHELXL 2012 incorporated into ShelXle.5 Single crystals of Eu$^{II}$-222FbCl$_2$ contained one cation of Eu$^{II}$-222FbCl and one chloride counter ion in the asymmetric unit. The structure was solved with a resolution of 0.59 Å in space group P121/n1. All non-hydrogen atoms were refined anisotropically. CCDC 1415606 contains the supplementary crystallographic data for this paper. These data are provided free of charge by The Cambridge Crystallographic Data Centre.

TABLE 3

Crystallographic properties of Eu$^{II}$-222FbCl$_2$.

| Chemical formula | C$_{22}$H$_{35}$Cl$_2$EuFN$_2$O$_6$ | |
|---|---|---|
| Formula weight | 665.38 | |
| Temperature | 100(2) K | |
| Wavelength | 0.71073 Å | |
| Crystal system | monoclinic | |
| Space group | P 1 21/n 1 | |
| Unit cell dimensions | a = 10.6274(9) Å | α = 90° |
|  | b = 17.8644(14) Å | β = 99.036(4)° |
|  | c = 13.6797(12) Å | γ = 90° |
| Volume | 2564.9(4) Å$^3$ | |
| Z | 4 | |
| Density (calculated) | 1.723 g cm$^{-3}$ | |
| Absorption coefficient | 2.701 mm$^{-1}$ | |
| F(000) | 1340 | |

2. Evaluation of Eu$^{II}$-Based Positive Contrast Enhancement After Intravenous, Intraperitoneal, and Subcutaneous Injections In vivo Eu$^{II}$-based contrast enhancement was evaluated in MRI after intravenous, intraperitoneal, and subcutaneous injections using Eu$^{II}$-222 (222=4,7,13,16,21,24-hexaoxa-1,10-diazabicyclo[8.8.8]hexacosane, Formula 1 counterions omitted). Biodistribution trends are also presented.

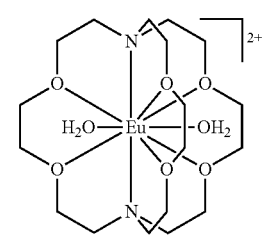

Figure 6:
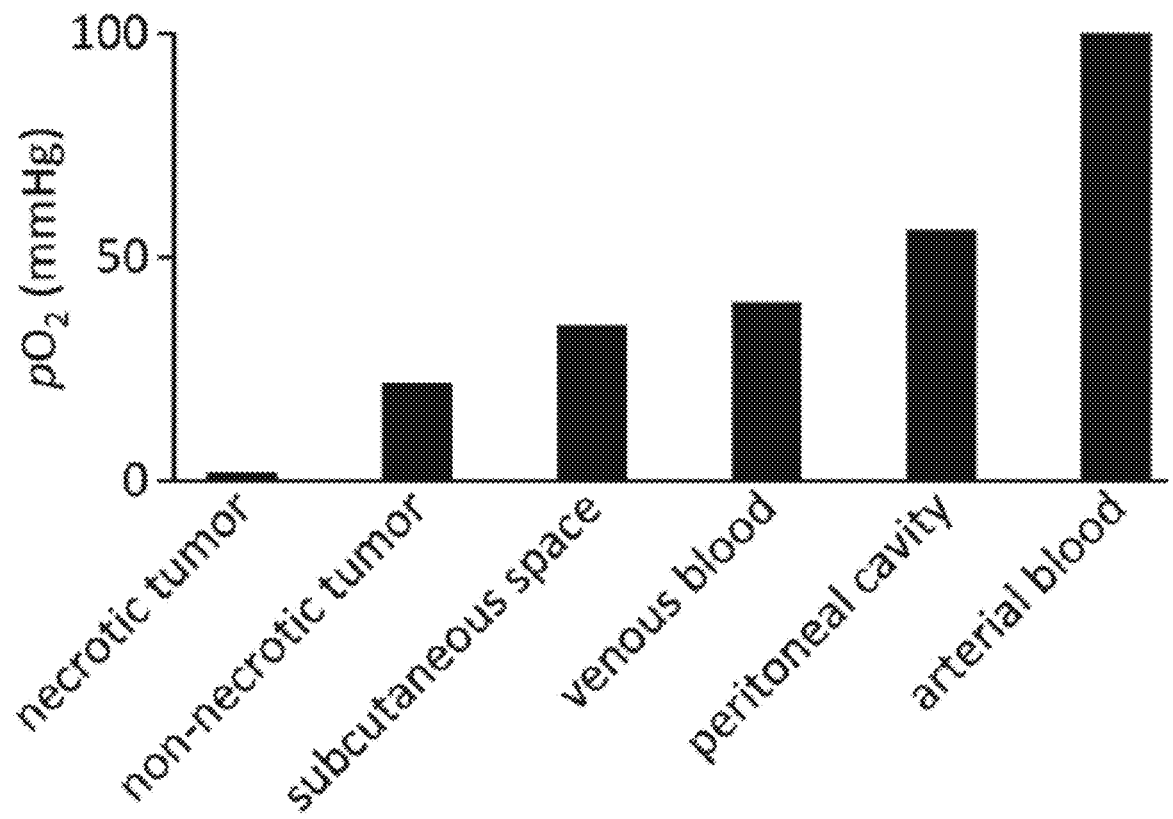
FIG. 6. $pO_2$ ranges in necrotic and non-necrotic tumor (converted from percent hemoglobin saturation using a hemoglobin saturation curve) subcutaneous space, venous blood, the peritoneal cavity, and arterial blood. (Hardee M E, Dewhirst M W, Agarwal N, Sorg B S. Novel imaging provides new insights into mechanisms of oxygen transport in tumors. Curr. Mol. Med. 2009; 9: 435-441. DOI: 10.2174/156652409788167122; Leow M K. Configuration of the hemoglobin oxygen dissociation curve demystified: a basic mathematical proof for medical and biological sciences undergraduates. Adv. Physiol. Educ. 2007; 31: 198-201. DOI: 10.1152/advan.00012.2007; Carreau A, Hafny-Rahbi B E, Matejuk A, Grillon C, Kieda C. Why is the partial oxygen pressure of human tissues a crucial parameter? Small molecules and hypoxia. J. Cell. Mol. Med. 2011; 15.
Figures 7D, 7E, 7F:
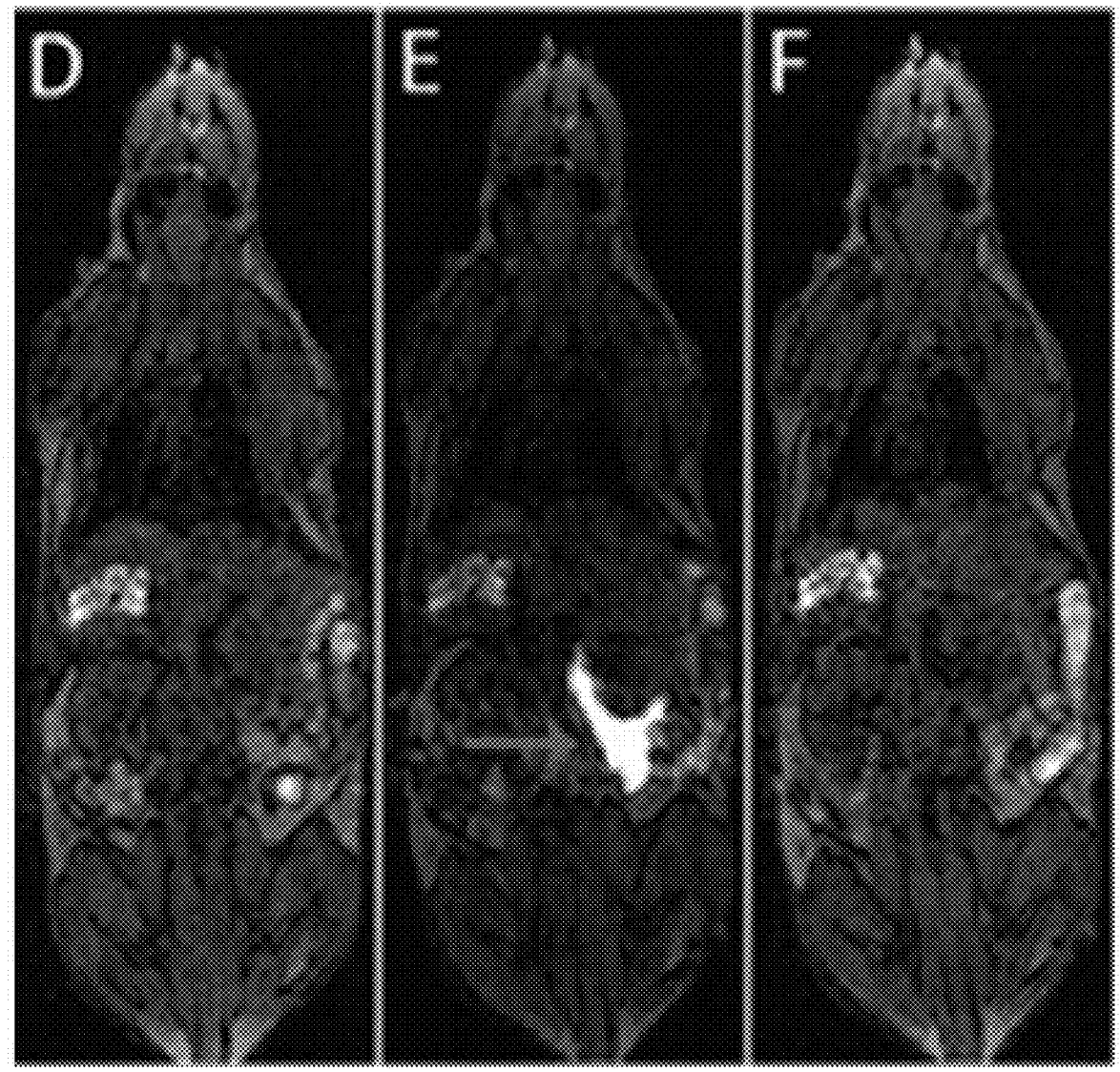
Figures 7G, 7H, 7I:
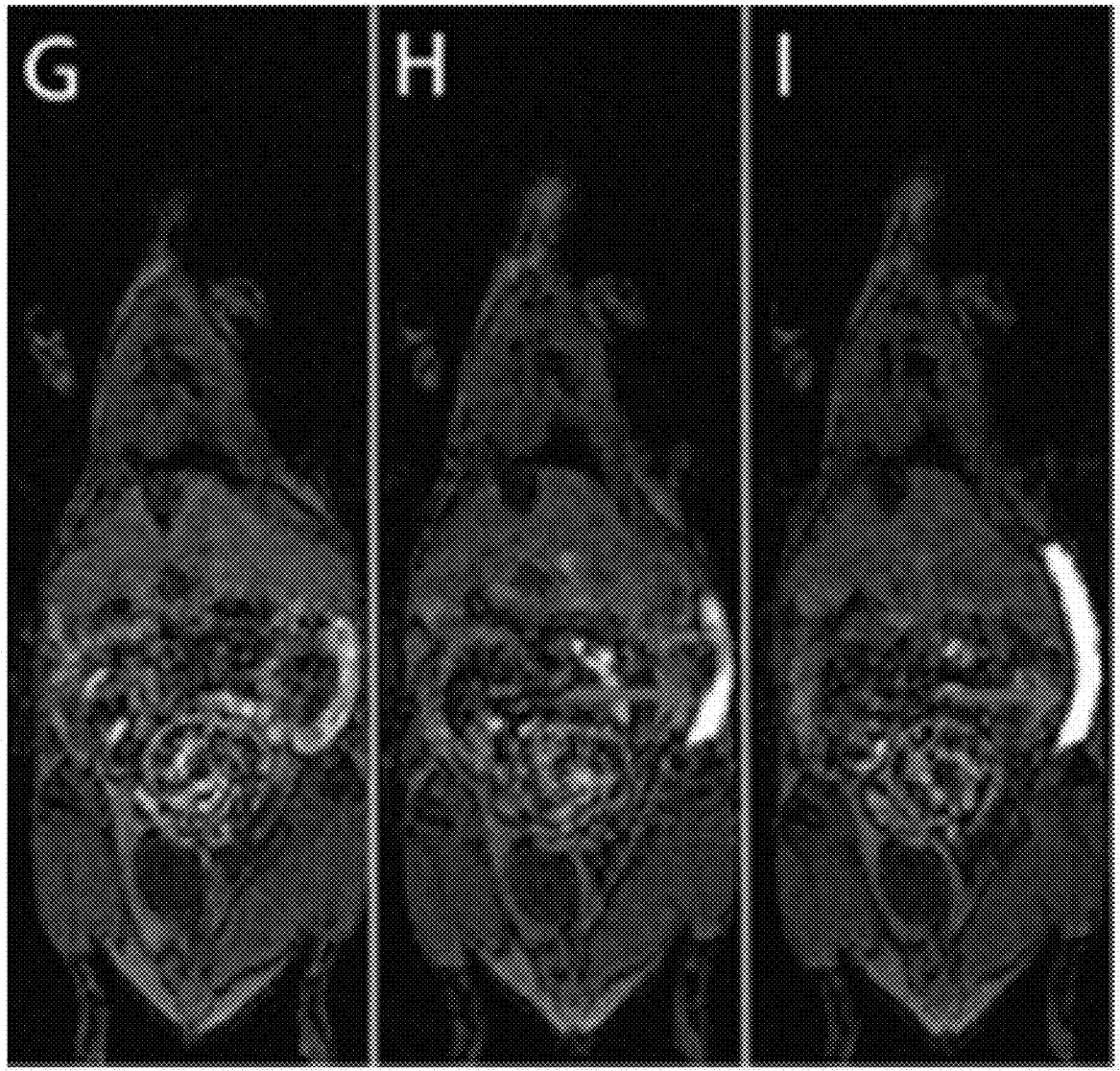

The ability of $Eu^{II}$-222 to impart oxidative stabilization of the +2 oxidation state of europium has been studied (28,29), and recent reports have characterized the aqueous magnetic and electrochemical properties of $Eu^{II}$-222 and other $Eu^{II}$-containing complexes (18-27,30-33). Despite increased oxidative stability, the $Eu^{II}$ ion of $Eu^{II}$-222 is prone to rapid oxidation by oxygen in solution (18). Oxidation of $Eu^{II}$ in elevated oxygen partial pressures coincides with the loss of positive contrast enhancement (19), and we suspected this change in contrast enhancement would be observable in vivo. The +2 oxidation state of europium has been demonstrated to persist for hours within relatively oxygen-deficient necrotic tissue ($pO_2 < 10$ mmHg) (18); therefore, we turned our attention to regions containing relatively higher levels of dissolved oxygen such as the subcutaneous space, fluids of the peritoneal cavity, and blood (FIG. 6).

Results and Discussion

To test our hypothesis regarding the in vivo response of $Eu^{II}$-222, we acquired $T_1$-weighted images of mice after administering $Eu^{II}$-222 (0.1 mL, 4 mM, europium dose of 3 mg/kg) through intravenous, intraperitoneal, and subcutaneous injections (FIG. 8). Mice were imaged prior to injection and at 3 and 8 min to compare responses with the three injection types. Based on these images, the intravenous injection resulted in no positive contrast enhancement; the intraperitoneal injection led to positive contrast enhancement in the peritoneal cavity that disappeared by 8 min; and the subcutaneous injection produced positive contrast enhancement both 3 and 8 min post-injection. The absence of positive contrast enhancement after the intravenous injection suggests that $Eu^{II}$-222 was oxidized within the first 3 min in the blood. Although this observation is inconsistent with the low oxygen content of venous blood (relative to the peritoneal cavity), the circulation time of blood in a mouse is approximately 8 s (38). This rapid circulation suggests that venous and arterial blood exchanged ~24 times over the course of the scan, allowing for blood solutes (including $Eu^{II}$-222) to be exposed to a relatively high level of oxygen. Therefore, the exchange between venous and arterial blood during circulation can explain our observations. It is unlikely that dilution alone could account for the complete loss of observable positive contrast enhancement because no positive contrast enhancement was observed in organs associated with clearance (liver, kidneys, or bladder; FIG. 7), whereas positive contrast enhancement was observed in the kidneys within 3 min after intravenous injection of an equivalent dose of $Gd^{III}$-diethylenetriaminepentaacetate. To ensure that $Eu^{II}$-222 had not been oxidized prior to the injection, we acquired $T_1$-weighted images of the syringe before and after the injection and observed positive contrast enhancement for both, indicating that oxidation occurred in vivo.

An intraperitoneal injection placed $Eu^{II}$-222 into an intermediate $pO_2$ range (relative to intravenous and subcutaneous injections) and allowed positive contrast enhancement to be observed in the 3 min scan. However, the loss of positive contrast enhancement by 8 min suggests that $Eu^{II}$-222 diffused to regions of high oxygen level (vasculature), oxygen diffused into the peritoneal cavity, or both types of diffusion occurred. Relative to the peritoneal cavity, subcutaneous space has a lower rate of diffusion and a lower $pO_2$ (36,37,39). Consistent with these properties, positive contrast enhancement was observed both 3 and 8 min post-subcutaneous injection. Results of the intravenous, intraperitoneal, and subcutaneous imaging experiments suggest that both $pO_2$ and diffusion play a role in the persistence of $Eu^{II}$-based contrast enhancement in vivo. Furthermore, despite oxidation occurring in the mice, no adverse effects were observed during any of the in vivo studies reported here.

The imaging data presented here demonstrate that $Eu^{II}$-222 is oxidized faster than the MRI timescale used in our experiments for intravenous injections, that intraperitoneal injections offer transitory contrast enhancement, and that subcutaneous injections exhibit positive contrast enhancement for at least 8 min. Our observed trends correlate with reported values of $pO_2$ (34-37), where lower $pO_2$ values correspond to prolonged contrast enhancement. The lack and loss of positive contrast enhancement observed in the intravenous and intraperitoneal injections, respectively, led us to measure the biodistribution of europium, which we suspected would be informative regarding the route of clearance.

To understand the biodistribution of europium for the intravenous and intraperitoneal injections, we used inductively coupled plasma mass spectrometry (ICP-MS) to quantify europium in the blood, liver, kidneys, spleen, heart, bone (femur), muscle (thigh), brain, upper and lower gastrointestinal tract (GI), stomach, lungs, and brain (FIG. 8). The majority of detected europium was found in the liver and kidneys for both types of injections, with the relative quantities being higher for intravenous injections. ICP-MS data does not provide insight into speciation during clearance, a complicated topic that we are investigating using knowledge of the kinetic stability of $Eu^{II}$-containing cryptates (29); however, ICP-MS data provide valuable insight into the route of clearance. For intraperitoneal injections, the smaller amount of europium detected in the liver, kidneys, and blood might indicate relatively slow diffusion from the peritoneal cavity. Evidence of slow diffusion of $Eu^{II}$-222 from the peritoneal cavity supports a response dependent on the diffusion of oxygen into the peritoneal cavity. Furthermore, the presence of europium in detectable quantities after intravenous injections (there is no endogenous europium in mice), together with the images in FIG. 7, suggest that oxidation of $Eu^{II}$-222 occurs within 3 min of intravenous injection.

Conclusions

Our results demonstrate that $Eu^{II}$-based contrast enhancement is sensitive to the route of administration, with positive contrast enhancement expected for regions containing relatively low levels of oxygen and slow rates of diffusion. These results help define the boundaries of $Eu^{II}$-based positive contrast enhancement with $Eu^{II}$-222 in vivo, and might be helpful in the preclinical application of other $Eu^{II}$-based complexes. Furthermore, the in vivo use of lanthanide-based redox-response is a relatively unexplored realm. Although other redox-active molecules might contribute to the oxidation of $Eu^{II}$, we expect that the oxidation of $Eu^{II}$ by oxygen is responsible for the correlation between oxygen content and the persistence of positive contrast enhancement in vivo, and efforts in our laboratory to understand aqueous $Eu^{II}$ oxidation chemistry are currently underway. Additionally, our biodistribution studies revealed clearance of europium through the liver and kidneys, but no positive contrast enhancement was observed in these organs. These results are an important step towards understanding the scope of $Eu^{II}$-based positive contrast enhancement for a new class redox-active contrast agents based on lanthanide redox chemistry.

EXPERIMENTAL

General Procedures

Commercially available chemicals were of reagent-grade purity or better and were used without further purification unless otherwise noted. Water was purified using a PURELAB Ultra Mk2 water purification system (ELGA) and degassed prior to use.

Preparation of Contrast Agent Solutions

Contrast agent solutions for intravenous, intraperitoneal, and subcutaneous injections were prepared by adding aqueous $EuCl_2$ and aqueous 4,7,13,16,21,24-hexaoxa-1,10-diazabicyclo[8.8.8]hexacosane (222) in a 1:1 ratio to a 4 mL glass vial equipped with a magnetic stir bar under an atmosphere of $N_2$. The resulting clear, colorless solution was stirred for 1 h before addition of the 10× phosphate buffered saline (PBS, Fisher BioReagents) and water to achieve a final solution of $Eu^{II}$-222 (4 mM) in PBS (11.9 mM phosphates, 137 mM NaCl, and 2.7 mM KCl). The clear, colorless solution was stirred for 30 min then filtered through a 0.2 μm hydrophilic filter. The concentration of europium in the clear, colorless filtrate was determined by ICP-MS and was used directly for imaging studies.

ICP-MS

ICP-MS measurements were acquired on an Agilent Technologies 7700 series spectrometer in the Lumigen Instrument Center at Wayne State University. All dilutions were performed with 2% $HNO_3$ that was also used for blank samples during calibration. The calibration curve was created using the $^{153}Eu$ isotope ion count for a 10-100 ppb concentration range (diluted from Fluka ICP standard solution, $Eu_2O_3$ in aqueous 2% $HNO_3$, 1000 mg Eu/L), and samples (with the exception of tissue digestion) were diluted to fall within this range.

Magnetic Resonance Imaging

Studies in animals were carried out with the assistance of the Animal Model and Therapeutics Evaluation Core of the Barbara Ann Karmanos Cancer Institute after approval from the Wayne State University Institutional Animal Care and Use Committee. MRI scans were performed in the Elliman Clinical Research Building at Wayne State University with a 7 T Bruker Clinscan small animal MRI scanner equipped with a 30 cm bore. $T_1$-weighted images (3D FLASH) were acquired with a body coil while using a warm water circulator set to 37° C. The whole body coronal plane images were acquired using an echo time of 1.5 ms, repetition time of 11 ms, flip angle of 40 degrees, 44 image slices at 0.5 mm thickness, and a 31 mm×90 mm field of view, and an in plane resolution of 0.352 mm×0.352 mm.

For intravenous injections, mice were catheterized before being anesthetized with isoflurane. A micro-volume extension set was used to inject the solution of $Eu^{II}$-222 into the tail vein without removing the mouse from the magnet. A correction volume (0.08 mL) was added to the calculated dose volumes for intravenous injections to account for the volume of the phosphate-buffered saline within the catheter. For intraperitoneal and subcutaneous injections, mice were first anesthetized with isoflurane, imaged prior to injection, and then the cradle with the mouse was removed from the magnet to perform the injection while still anesthetized. After injections, mice were imaged immediately to acquire the first time points post-injection. Intravenous injections were triplicated, intraperitoneal injections were duplicated, and the subcutaneous injection was performed once.

Biodistribution Studies

For biodistribution studies, mice were not catheterized or anesthetized. Mice were injected with the same europium dose used for imaging (3 mg/kg) before being sacrificed 1 h post-injection at which point the blood, liver, kidneys, spleen, heart, bone (femur), muscle (thigh), brain, upper and lower GI tract, stomach, and lungs were harvested. The samples were weighed, freeze dried for 72 h, and digested in 25 mL volumetric flasks using 6 mL of 3 M nitric acid at 75° C. with constant stirring for 16 h. The entirety of each sample was used for digestion with the exception of the liver, which was homogenized with mortar and pestle prior to addition to a volumetric flask and a fraction (~130 mg) of the homogenate was added to a volumetric flask. After 16 h, the digests were allowed to cool to ambient temperature before the addition of water to achieve a total volume of 25 mL. The digests were transferred to conical tubes (50 mL) and insoluble oils were removed by centrifugation. The clear, yellow supernatants were immediately transferred to conical tubes (15 mL) for analysis of europium concentration with ICP-MS.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of magnetic resonance imaging a target tissue in a subject, the method comprising:
    a) administering a first $Eu^{2+}$-containing complex to the subject, the first $Eu^{2+}$-containing complex having a reduction potential that is more negative than a reduction potential for a selected compound present in the target tissue;
    b) taking a first set of images of the target tissue in the subject by $T_1$-weighted magnetic resonance imaging;
    c) administering a second $Eu^{2+}$-containing complex to the subject, the second $Eu^{2+}$-containing complex having a reduction potential that is more positive than a reduction potential for the selected compound present; and
    d) taking a second set of images of the target tissue in the subject by $T_1$-weighted magnetic resonance imaging.

2. The method of claim 1 wherein the first $Eu^{2+}$-containing complex includes a europium metal ion ($Eu^{2+}$) and a multi-dentate ligand selected from the group consisting of cryptands and thiacryptands and counter-ions to maintain charge neutrality.

3. The method of claim 2 wherein the multi-dentate ligand is described by formula I:

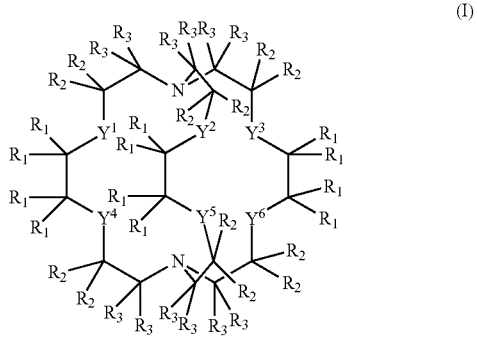

wherein:

$Y^1, Y^2, Y^3, Y^4, Y^5$ and $Y^6$ are each independently O or S;

$R_1, R_2, R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by combining $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom; and R is H or $C_{1-12}$ alkyl.

4. The method of claim 2 wherein $R_1$, $R_2$, or $R_3$ are each independently H, phenyl, or biphenyl.

5. The method of claim 1 wherein the first $Eu^{2+}$-containing complex and the second $Eu^{2+}$-containing complex to the subject are administered by intravenous, intraperitoneal, or subcutaneous injection.

6. The method of claim 1 wherein the second $Eu^{2+}$-containing complex includes a europium metal ion ($Eu^{2+}$) and a multi-dentate ligand selected from the group consisting of cryptands and thiacryptands and counter-ions to maintain charge neutrality.

7. The method of claim 6 wherein the multi-dentate ligand is described by formula I:

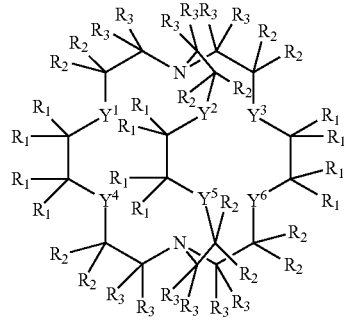

(I)

wherein:

$Y^1, Y^2, Y^3, Y^4, Y^5$ and $Y^6$ are each independently O or S;

$R_1, R_2, R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by combining $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom; and R is H or $C_{1-12}$ alkyl.

8. The method of claim 1 wherein the target tissue is necrotic tissue.

9. A method of magnetic resonance imaging a target tissue in a subject, the method comprising:

a) administering a first $Eu^{2+}$-containing complex to the subject, the first $Eu^{2+}$-containing complex having a reduction potential that is more negative than a reduction potential for a selected compound present in the target tissue;

b) taking a first set of images of the target tissue in the subject by $T_1$-weighted magnetic resonance imaging;

c) administering a second $Eu^{2+}$-containing complex to the subject, the second $Eu^{2+}$-containing complex having a reduction potential that is more positive than a reduction potential for the selected compound present;

d) taking a second set of images of the target tissue in the subject by $T_1$-weighted magnetic resonance imaging; and e) comparing the first set of images and the second set of images to identify regions that possess different concentrations of the selected compound.

10. The method of claim 9 wherein the first $Eu^{2+}$-containing complex and the second $Eu^{2+}$-containing complex each independently include a europium metal ion ($Eu^{2+}$) and a multi-dentate ligand selected from the group consisting of cryptands and thiacryptands and counter-ions to maintain charge neutrality.

11. The method of claim 10 wherein the multi-dentate ligand is described by formula I:

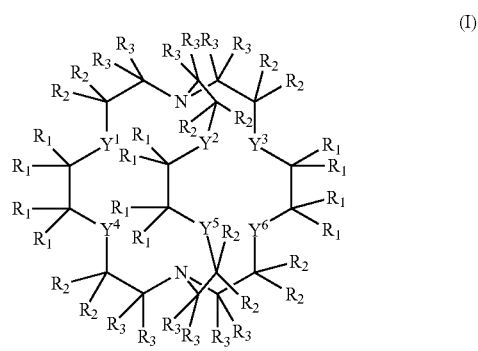

(I)

wherein:

$Y^1, Y^2, Y^3, Y^4, Y^5$ and $Y^6$ are each independently O or S;

$R_1, R_2, R_3$ are each independently H, $C_{1-12}$ alkyl, $C_{1-12}$ alkynyl, $C_{1-12}$ alkenyl, $C_{1-12}$ fluoroalkyl, Cl, F, Br, nitro, cyano, or $C_{6-14}$ aryl, $C_{5-14}$ hetereoaryl, or 5 and 6 membered rings formed by combining $R_1$ on adjacent carbon atoms or $R_2$ and $R_3$ on adjacent carbon atoms, =O by combining $R_1$, $R_2$, or $R_3$ on the same carbon atom, =S by combining $R_1$, $R_2$, or $R_3$ on the same carbon atom, or =NR by combining $R_1$, $R_2$, or $R_3$ on the same carbon atom; and R is H or $C_{1-12}$ alkyl.

12. The method of claim 11 wherein $R_1$, $R_2$, or $R_3$ are each independently H, phenyl, or biphenyl.

13. The method of claim 9 wherein the a first $Eu^{2+}$-containing complex and the second $Eu^{2+}$-containing complex to the subject are administered by intravenous, intraperitoneal, or subcutaneous injection.

14. The method of claim 9 wherein the target tissue is necrotic tissue.

15. The method of claim 2 wherein $R_2$ and $R_3$ are hydrogen and one of the $R_1$ is not hydrogen. In other refinements, $R_2$ and $R_3$ are hydrogen and two of the $R_1$ are not hydrogen.

16. The method of claim 2 wherein $R_2$ and $R_3$ are hydrogen and two of the $R_1$ are not hydrogen.

17. The method of claim 11 wherein $R_2$ and $R_3$ are hydrogen and one of the $R_1$ is not hydrogen. In other refinements, $R_2$ and $R_3$ are hydrogen and two of the $R_1$ are not hydrogen.

18. The method of claim 11 wherein $R_2$ and $R_3$ are hydrogen and two of the $R_1$ are not hydrogen.

* * * * *